(12) United States Patent
Williamson et al.

(10) Patent No.: US 11,524,080 B2
(45) Date of Patent: Dec. 13, 2022

(54) METHODS FOR THE PREPARATION OF A PHARMACEUTICAL-VESICLE FORMULATION AND ASSOCIATED PRODUCTS AND USES

(71) Applicants: THE SECRETARY OF STATE FOR DEFENCE, Salisbury (GB); THE UNIVERSITY OF STRATHCLYDE, Glasgow (GB)

(72) Inventors: Ethel Diane Williamson, Salisbury (GB); Riccardo Vincenzo D'Elia, Salisbury (GB); Craig William Roberts, Glasgow (GB); Stuart Woods, Glasgow (GB)

(73) Assignees: The Secretary of State for Defence, Salisbury (GB); The University of Strathclyde, Glasgow (GB)

( * ) Notice: Subject to any disclaimer, the term of this patent is extended or adjusted under 35 U.S.C. 154(b) by 0 days.

(21) Appl. No.: 17/273,059

(22) PCT Filed: Sep. 13, 2019

(86) PCT No.: PCT/GB2019/000134
§ 371 (c)(1),
(2) Date: Mar. 3, 2021

(87) PCT Pub. No.: WO2020/053541
PCT Pub. Date: Mar. 19, 2020

(65) Prior Publication Data
US 2021/0316009 A1    Oct. 14, 2021

(30) Foreign Application Priority Data
Sep. 14, 2018 (GB) .................................. 1814959

(51) Int. Cl.
*A61K 47/69* (2017.01)
*A61K 47/54* (2017.01)
(Continued)

(52) U.S. Cl.
CPC ........ *A61K 47/6911* (2017.08); *A61K 9/1272* (2013.01); *A61K 9/1277* (2013.01);
(Continued)

(58) Field of Classification Search
CPC A61K 47/6911; A61K 9/1272; A61K 9/1277; A61K 31/496; A61K 31/513;
(Continued)

(56) References Cited

U.S. PATENT DOCUMENTS

2005/0084523 A1    4/2005  Shafer et al.
2014/0356399 A1*  12/2014  Anderson ............... A61P 37/04
                                                       424/224.1
(Continued)

FOREIGN PATENT DOCUMENTS

EP    2451950 A1    5/2012
EP    2590674 A2    5/2013
(Continued)

OTHER PUBLICATIONS

Pawar, S. K., et al in International Journal of Pharmaceutics, vol. 436, Issues 1-2, Oct. 2012, pp. 183-193.*
(Continued)

*Primary Examiner* — Gollamudi S Kishore
(74) *Attorney, Agent, or Firm* — Kilpatrick Townsend & Stockton LLP

(57) ABSTRACT

The invention relates to methods for the preparation of a pharmaceutical-vesicle formulation comprising steps of: preparing and processing vesicle components and a pharmaceutical agent to entrap the pharmaceutical agent in the vesicle and form a pharmaceutical-vesicle formulation,
(Continued)

wherein the pharmaceutical-vesicle formulation is reconstituted in a known quantity of the pharmaceutical agent dissolved in a pharmaceutically-acceptable carrier to provide a biphasic pharmaceutical-vesicle formulation. The invention also relates to the associated pharmaceutical-vesicle formulations, pharmaceutical kits and uses as a medicament, in particular for the prevention or treatment of infection by bacteria such as *Burkholderia pseudomallei* and *Francisella tularensis*, and viruses such as Venezuelan Equine Encephalitis Virus (VEEV).

19 Claims, 14 Drawing Sheets

Specification includes a Sequence Listing.

(51) Int. Cl.

| | | |
|---|---|---|
| *A61P 31/14* | (2006.01) | |
| *A61P 31/04* | (2006.01) | |
| *A61K 9/127* | (2006.01) | |
| *A61K 31/496* | (2006.01) | |
| *A61K 31/513* | (2006.01) | |
| *A61K 31/5383* | (2006.01) | |
| *A61K 31/65* | (2006.01) | |
| *A61K 31/711* | (2006.01) | |
| *A61K 38/21* | (2006.01) | |
| *A61K 47/14* | (2017.01) | |
| *A61K 47/24* | (2006.01) | |
| *A61K 47/26* | (2006.01) | |
| *A61K 47/28* | (2006.01) | |
| *A61K 47/42* | (2017.01) | |
| *C07K 16/10* | (2006.01) | |

(52) U.S. Cl.
CPC .......... *A61K 31/496* (2013.01); *A61K 31/513* (2013.01); *A61K 31/5383* (2013.01); *A61K 31/65* (2013.01); *A61K 31/711* (2013.01); *A61K 38/212* (2013.01); *A61K 38/217* (2013.01); *A61K 47/14* (2013.01); *A61K 47/24* (2013.01); *A61K 47/26* (2013.01); *A61K 47/28* (2013.01); *A61K 47/42* (2013.01); *A61K 47/545* (2017.08); *A61P 31/04* (2018.01); *A61P 31/14* (2018.01); *C07K 16/1081* (2013.01)

(58) Field of Classification Search
CPC .. A61K 31/5383; A61K 31/65; A61K 31/711; A61K 38/212; A61K 38/217; A61K 47/14; A61K 47/24; A61K 47/26; A61K 47/28; A61K 47/42; A61K 47/545; A61K 2039/505; A61K 2039/54; A61K 9/0095; A61K 9/1623; A61K 9/19; A61K 39/395; A61K 9/0053; A61P 31/04; A61P 31/14; A61P 31/12; C07K 16/1081; C07K 2317/24

See application file for complete search history.

(56) References Cited

U.S. PATENT DOCUMENTS

| | | | |
|---|---|---|---|
| 2015/0037352 A1* | 2/2015 | Shriver | A61P 37/02 435/339 |
| 2015/0182636 A1* | 7/2015 | Ennis | A61P 43/00 424/93.21 |
| 2016/0058864 A1* | 3/2016 | Meehan | A61K 47/545 544/193.2 |
| 2016/0228573 A1* | 8/2016 | Niyikiza | A61K 9/1271 |

FOREIGN PATENT DOCUMENTS

| | | |
|---|---|---|
| EP | 3060198 A1 | 8/2016 |
| EP | 3129008 A1 | 2/2017 |
| WO | 9704768 A1 | 2/1997 |
| WO | 2011005769 A1 | 1/2011 |
| WO | 2011005772 A1 | 1/2011 |
| WO | 2011036435 A1 | 3/2011 |
| WO | 2013072768 A2 | 5/2013 |
| WO | 2013111012 A2 | 8/2013 |
| WO | 2015061025 A1 | 4/2015 |
| WO | 2015156904 A1 | 10/2015 |

OTHER PUBLICATIONS

Sancho, M., et al in Colloids and Surfaces B: Biointerfaces, vol. 1, pp. 373-381, 1993.*
United Kingdom Patent Application No. GB1814959.1, Search Report dated Mar. 11, 2019, 5 pages.
International Patent Application No. PCT/GB2019/000134, International Search Report and Written Opinion dated Jan. 3, 2020, 16 pages.
United Kingdom Patent Application No. GB1913128.3, Combined Search and Examination Report dated Feb. 26, 2020, 4 pages.
Bennett et al., "Translational modifications to improve vaccine efficacy in an oral influenza vaccine," Methods, 2009, pp. 322-327, vol. 49, Elsevier Inc.
Xie et al., "Regulatory roles of c-jun in H5N1 influenza virus replication and host inflammation," Biochimica et Biophysica Acta, 2014, pp. 2479-2488, vol. 1842, Elsevier B.V.
Goodchild et al., "A humanised murine monoclonal antibody with broad serogroup specificity protects mice from challenge with Venezuelan equine encephalitis virus," Antiviral Research, 2011, pp. 1-8, vol. 90, Elsevier B.V.
International Patent Application No. PCT/GB2019/000134, International Preliminary Report on Patentability dated Mar. 25, 2021, 9 pages.

* cited by examiner

Fig. 3
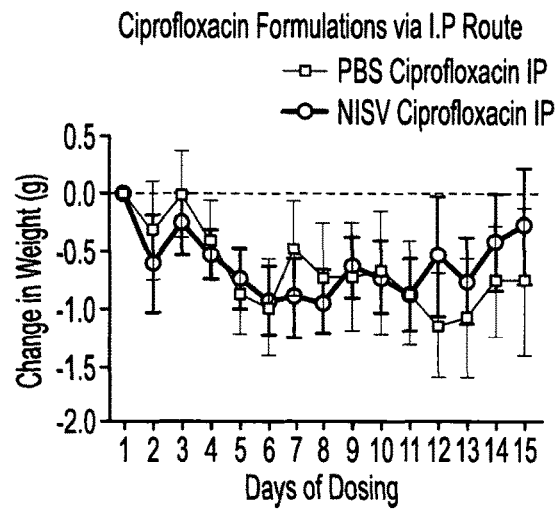
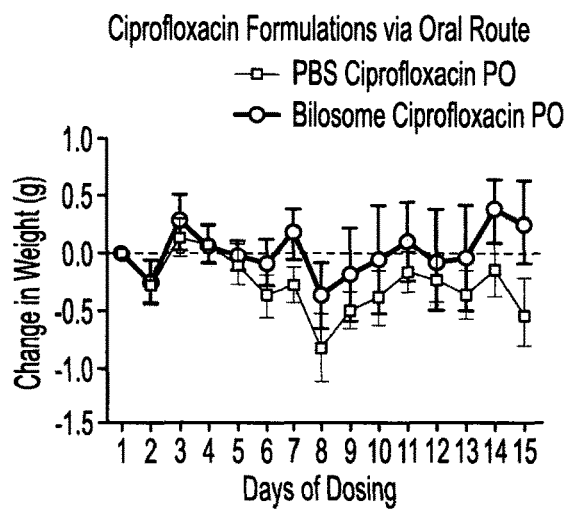
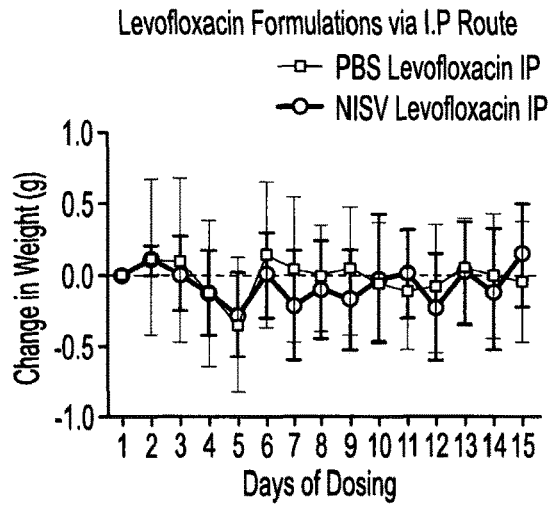
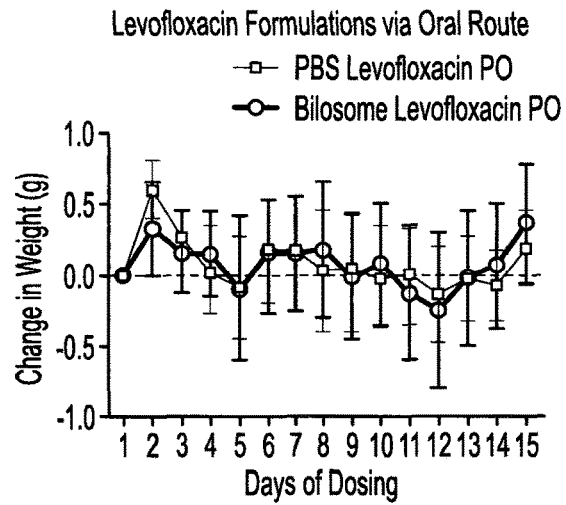
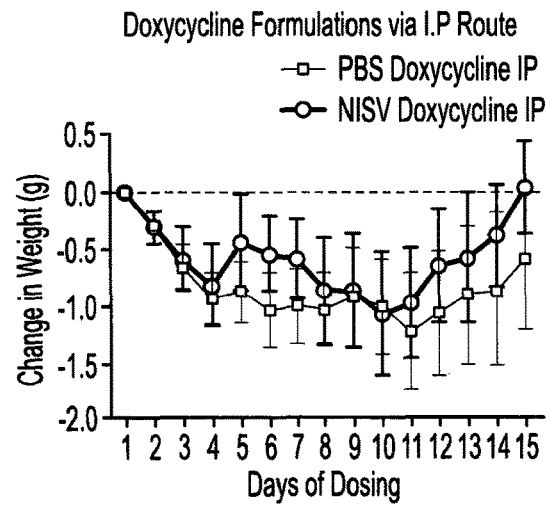
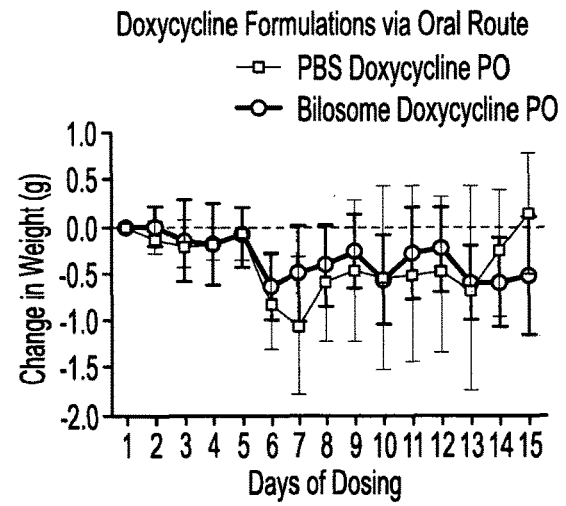

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
gtgccagcmg ccgcggtaa                    19

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ggactachvg ggtwtctaat                   20

METHODS FOR THE PREPARATION OF A PHARMACEUTICAL-VESICLE FORMULATION AND ASSOCIATED PRODUCTS AND USES

TECHNICAL FIELD OF THE INVENTION

The invention relates to methods for the preparation of a pharmaceutical-vesicle formulation, and associated pharmaceutical-vesicle formulations, pharmaceutical kits and uses as a medicament, in particular for the prevention or treatment of infection by bacteria such as *Burkholderia pseudomallei* and *Francisella tularensis*, and viruses such as Venezuelan Equine Encephalitis Virus (VEEV). The invention relates in particular to methods of preparing pharmaceutical-vesicle formulations comprising Non-Ionic Surfactant Vesicles (NISVs), or modified vesicles thereof, which entrap pharmaceutical agents including antibiotics such as levofloxacin, doxycycline or ciprofloxacin and antivirals such as humanised anti-VEEV monoclonal IgG Hu1A3B-7.

BACKGROUND TO THE INVENTION

Antimicrobial agents, encompassing antibiotics and antivirals effective against bacteria and viruses respectively, continue to be one of the most commonly deployed strategies for resolving infections in an animal host. However, the emergence of antimicrobial resistance, along with the natural ability of microbes to evade treatment, is a continuing concern. Furthermore, it is well documented that there has been a lack of investment in new antimicrobial therapies.

*Burkholderia pseudomallei* is an environmental Gram-negative bacterium and the causative agent of the human disease melioidosis. *B. pseudomallei* is endemic to tropical regions such as Thailand and Northern Australia and particularly associated with wet conditions such as paddy fields. Human exposure can occur via routes that include through the skin, for example as a result of scratches or other lesions, leading to an acute febrile illness depending on the inoculum size. The bacteria can also infect humans via inhalation, resulting in a more acute pneumonic infection.

*F. tularensis* is considered an intracellular pathogen and the causative agent of the disease tularemia. Although typical zoonotic hosts of *F. tularensis* include rodents and lagomorphs, incidents of tularemia in humans are documented. Of the four known subspecies of *F. tularensis* (*tularensis, holarctica, mediasiatica* and *novicida*), *F. tularensis* subspecies *tularensis* is considered the most clinically relevant subspecies, capable of infecting humans with a low infectious dose, in particular via the respiratory route (<50 colony forming units).

The alpha-virus VEEV is capable of causing disease in animals including horses and humans, and is transmitted via arthropod vectors such as mosquitos and ticks. VEEV has been associated with historic use as a biological warfare agent.

Microbiological agents such as *B. pseudomallei, F. tularensis* and VEEV all present challenges for the development of effective medical countermeasures. Both *B. pseudomallei* and *F. tularensis* have developed mechanisms to evade innate immune defences and persist within a host environment. In particular, *B. pseudomallei* has evolved multiple secretory and other immunomodulatory mechanisms to enable survival within intracellular granulomatous lesions for long periods, thus making this pathogen extremely difficult to access and treat effectively. Indeed, one documented case has described human infection of *B. pseudomallei* re-emerging 60 years after the original exposure. Similarly viruses, such as VEEV, are notoriously difficult to treat due to their need to replicate within host cells. The ability to treat encephalitic viruses is further complicated when the virus accesses and replicate in the brain, an in vivo site protected by the blood brain barrier (BBB).

There are currently no fully licensed vaccines against melioidosis tularemia or VEEV. As a consequence, there is a heavy reliance on existing antimicrobial agents to treat infection. However, the following examples highlight limiting factors that may impact on the use of existing antimicrobial agents to clear such infections.

*B. pseudomallei* is known to actively export antibiotics by efflux pumps, thus making this bacterium resistant to multiple antibiotics and very difficult to treat effectively in vivo. Indeed, data suggests that single antibiotic dosing regimens are only partially effective against *B. pseudomallei*. One option for improved efficacy against melioidosis is the application of combination therapy i.e. administering a plurality of antibiotics such as a β-lactam and a cephalosporin for the acute phase, to prevent overwhelming sepsis and mortality, and a mixture of antibiotics such as co-trimoxazole and the bacteriostatic broad-spectrum antibiotics chloramphenicol and doxycycline for an oral eradication phase to kill residual bacteria. However, such approaches risk side effects that may arise from such antibiotic combinations.

Antibiotic treatment of tularemia infection is also dependent on the correct selection of antibiotic. For example, β-lactams and macrolides are unsuitable. While aminoglycosides can be effective, administering such antibiotics can be impractical due to the requirement for the parenteral dosing and for monitoring of serum levels for toxicity. Although ciprofloxacin can be a preferred antibiotic for treatment of tularemia, data from murine models and incidents of human infection have suggested this regimen is not optimal due to relapse of infection once antibiotic dosing has ceased.

There are currently no licensed antivirals for VEEV. Viruses are notoriously more difficult to treat compared to bacterial pathogens due to their need to replicate within host cells. As common viral targets are also difficult to identify due to the vast variety of viruses (e.g. DNA, RNA, enveloped), antivirals therefore tend to be useful only against a specific viral family or genus. A broader approach may be achieved by targeting host-specific responses to viral infection. However, such therapies, including those for VEEV, are not yet optimized.

Thus, given the concern in general regarding antibiotic resistance among microbes such as bacteria, and the potential for selected treatment regimens to confer undesired side effects, there is a need for effective, safe and well-tolerated treatments of diseases. There is also a desire to optimise delivery of antimicrobial agents to particular intracellular niches to benefit treatment of pathogens. Such needs are apparent for infection by *B. pseudomallei, F. tularensis* and VEEV respectively.

SUMMARY OF THE INVENTION

The present invention provides a method for the preparation of a pharmaceutical-vesicle formulation, the method comprising the steps of: a) heating vesicle components comprising a surfactant, a hydrophobic substance and an amphiphile in the present or absence of an organic solvent; b) dissolving a pharmaceutical agent in a pharmaceutically-acceptable carrier and heating the resultant pharmaceutical agent-carrier mixture; c) adding the heated pharmaceutical agent-carrier mixture to the heated vesicle components to provide a formulation mixture; and d) processing the formulation mixture to entrap the pharmaceutical agent and carrier in a vesicle, the vesicle comprising the vesicle components, to form a pharmaceutical-vesicle formulation; wherein the pharmaceutical-vesicle formulation is reconstituted, prior to use, in a pharmaceutically-acceptable carrier. The concentration of the pharmaceutical agent entrapped within the vesicle can be measured prior to reconstitution. Furthermore, the pharmaceutical-vesicle formulation can be reconstituted, prior to use, in a known quantity of the pharmaceutical agent dissolved in a pharmaceutically-acceptable carrier to provide a biphasic pharmaceutical-vesicle formulation.

According to a first aspect, the invention provides a method for the preparation of a pharmaceutical-vesicle formulation, the method comprising the steps of: a) heating vesicle components comprising monopalmitoyl glycerol, cholesterol and dicetyl phosphate at a temperature in the range of 50° C. to 150° C.; b) dissolving a pharmaceutical agent in a pharmaceutically-acceptable carrier and heating the resultant pharmaceutical agent-carrier mixture at a range of 30-99° C.; c) adding the pharmaceutical agent-carrier mixture to the vesicle components to provide a formulation mixture; and d) processing the formulation mixture to form a pharmaceutical-vesicle formulation, whereby the pharmaceutical agent and carrier is entrapped within a plurality of vesicles; wherein the pharmaceutical-vesicle formulation is reconstituted in a known quantity of the pharmaceutical agent dissolved in a pharmaceutically-acceptable carrier to provide a biphasic pharmaceutical-vesicle formulation.

The term 'vesicle' as understood by the skilled person may refer to a nano- or micro-particulate structure capable of entrapping or associating with a compound or substance, such as a pharmaceutical agent. While the term 'entrapped' is used to describe the association between the pharmaceutical agent and the vesicles, it is envisaged that pharmaceutical agent may also be associated with the vesicles as a result of being bound to the vesicle surface.

The term 'pharmaceutical agent' refers to one, or at least one (i.e. encompassing more than one), component capable of inducing a biological effect on an animal, in particular a biological effect on tissue or cell(s) within the animal. The term 'pharmaceutical agent' includes therapeutic constituents suitable for use in the prevention or treatment of disease in an animal, for example drugs such as antibiotics, antivirals and/or biological molecules such as an antibody capable of recognising or binding to a pathogen, and/or other biological molecules capable of performing as vaccines, such as an element (e.g. protein, glycoprotein) expressed by a particular biological agent such as bacteria, yeast or virus, and particularly those biological entities considered to be pathogens capable of causing disease. Examples of disease include, but are not limited to, infection (for example infection caused by a bacterial or viral pathogen), cancer, inflammatory dysfunction (for example arthritis), diabetes, and/or allergies. The term 'pharmaceutical agent' can include agents that can act to ameliorate the animal's condition by modifying the animal's immune response in order to counteract the disease.

The term 'pharmaceutical agent' may refer to an immunogenic component with the ability to stimulate an immune response in an animal, such as a human. Such an immune response may be a systemic and/or mucosal immune response, for example in the gut and/or lung mucosa, which may stimulate a humoral and/or cell-mediated immune response. An immunogenic component may represent an epitope or target ('antigen') associated with a specific agent, for example a peptide, polypeptide, protein, glycoprotein, polysaccharide, nucleic acid or any variant or fragment thereof associated with an agent such as a bacterium or virus capable of causing disease in an animal. An immunogenic component may be an antigen, including a recombinant antigen, capable of stimulating, or assisting in stimulating, an agent-specific immune response in an animal.

The term 'pharmaceutically-acceptable carrier' refers to a substance in which the pharmaceutical agent can be mixed, for example a liquid capable of mixing with the pharmaceutical agent to provide a solution or emulsion, and which is suitable for administrating the pharmaceutical agent, for example in vivo. The term 'pharmaceutically acceptable carrier' encompasses substances known to the skilled person such as phosphate buffered saline (PBS). Preferably, the pharmaceutical carriers in the biphasic formulation (i.e. entrapped within the vesicles and used to reconstitute the formulation respectively) are the same pharmaceutical carrier.

The term 'pharmaceutical-vesicle formulation' refers to a plurality of vesicles, formed from the vesicle components, within which is entrapped (i.e. entrapped and/or bound) a pharmaceutical agent in a pharmaceutically-acceptable carrier.

With respect to method steps a) and b), it is to be understood that heating temperatures are to be used that are not detrimental to the components being heated. For step a), the vesicle components may be heated at a temperature of approximately 130° C. However, methods encompassing the use of off-the-shelf automated laboratory equipment (for example microfluidics devices such as Precision Nanosystem's Nanoassemblr®) may utilise lower temperatures, for example 65° C. For step a) conducted at lower temperatures, the vesicle components may be heated in the presence of an organic solvent, for example methanol at 100% concentration.

Preferably, the heating temperature with respect to method step b) is 50° C. to 60° C., in particular 60° C.

The term 'processing' with respect to step d) includes laboratory processes such as the following-non-limiting examples, to enable the provision of vesicles entrapping the pharmaceutical agent from the vesicle components/pharmaceutical agent-carrier mixture.

The formulation mixture may be processed by agitation and subsequent pelleting. The processes of agitation by vortexing could be applied, for example for 2 minutes at 2500 rpm. Alternatively, using a probe homogeniser can be used. Subsequent concentration of the formulation mixture could be achieved by centrifugation. Preferably, the formulation mixture is pelleted by ultracentrifugation, for example at 100,000×g for 1 hour. Alternatively, pelleting can be achieved through size exclusion filtration, such as using a spin column. The spin column approach is particularly suited for vesicles prepared on automated laboratory equipment. For example, vesicles prepared on the Nanoassemblr® can be separated from unentrapped drug by VivaSpin columns.

Following processing, preferably the concentration of the pharmaceutical agent entrapped within the vesicle is measured, for example by High Performance Liquid Chromatography (HPLC), Bradford assay or ninhydrin assay.

The term 'biphasic pharmaceutical-vesicle formulation' refers to a formulation designed in a manner that an amount of the pharmaceutical agent is entrapped (i.e. bound and/or entrapped) within vesicles, while the remaining pharmaceutical agent is free (i.e. not bound and/or entrapped within the vesicles) in an aqueous solution in which the vesicles are suspended. Biphasic pharmaceutical-vesicle formulations are typically prepared by re-suspending vesicles with bound/entrapped pharmaceutical agent in a pre-determined concentration of the same pharmaceutical agent in solution. The preferred combination is a 50/50 ratio of bound/entrapped to free antibiotic or that which is necessary to achieve equilibrium or a stable formulation.

The inventors have successfully generated methods for production of a pharmaceutical-vesicle formulation, requiring optimising an approach of binding and/or entrapping a pharmaceutical agent within a vesicle carrier, and demonstrating by iterative testing that such formulations offer improved pharmaceutical delivery and efficacy in vivo relative to the same pharmaceutical agent delivered in the absence of the vesicle carrier.

The method of the invention provides for the production of biocompatible and biodegradable vesicles, to which a pharmaceutical agent of choice can be bound and/or entrapped, and provides a platform technology for the delivery of said pharmaceutical agent to an animal. The physical properties of the vesicles have been shown by the inventors to confer a series of advantages including: enhancing cellular uptake of a pharmaceutical agent; being amenable to modification to achieve tissue-targeted drug delivery, e.g. a niche(s) where a pathogen may reside thus helping to aid total pathogen clearance; increased bioavailability; being inexpensive to synthesize; and amenable to lyophilisation.

Surprisingly, the method of the invention provides a delivery system, in particular an oral delivery system, which improves the delivery and efficacy of orally-availably pharmaceutical agents, including orally-available antibiotics. Furthermore, the method provides a delivery system with an unexpected and highly significant benefit in protection against pharmaceutical side effects, in particular antibiotic-induced weight loss. Thus, the vesicle platform has potential for exploitation for the oral delivery not only of antimicrobials, but also for a range of other therapeutics which may cause detrimental side-effects or require enhanced delivery.

The inventors have also shown that the method of the invention has the capability to entrap (i.e. bind and/or entrap) a variety of different antimicrobial agents in vesicles. Biphasic formulations were developed and assessed for stability in liquid and freeze-dried forms at multiple temperatures and time points. For example, optimised formulations of antibiotics using the method have been demonstrated to retain stability when held at −20° C. and full antimicrobial activity in vitro with values for Minimum Inhibitory Concentration (MIC) and Minimum Bactericidal Concentration (MBC) which do not differ from unformulated antibiotics. The stability of the freeze-dried biphasic formulations, at all temperatures tested and for three months duration stored in a lyophilised state, highlights a realistic concept of use. Stability of adapted and/or novel therapeutic formulations is of increasing interest, especially when distributed to low-to-middle income countries (LMIC) where cold storage may not be readily available.

Overall, the methods devised by the inventors have been shown to enable production of vesicle platform technologies that are very adaptable to modification to aid delivery and can provided clear survival advantages in terms of efficacy of a pharmaceutical agent in vivo, compared to free (i.e. not bound and/or entrapped to a vesicle carrier) pharmaceutical agent. Furthermore, the invention significantly protects against the side effects (principally weight loss) arising from repeated dosing.

The vesicles of the invention are NISVs, for example as described in PCT/GB96/01861 which discloses use of empty NISVs as a therapeutic agent against conditions with elevated cytokines, or modified NISVs. As understood by the skilled person, such vesicles comprise: a surfactant i.e. a compound capable of forming the NISV as a result of water-insoluble (or oil-soluble) and water-soluble components forming aggregates, such as micelles, in solution; a hydrophobic substance capable of mixing with the surfactant to form a bi-layer on which the physical properties of the vesicle depends; and a charge-producing amphiphile to cause the vesicle to take on a negative charge, helping to stabilise the vesicles and provide effective dispersion.

With respect to the invention, the selected vesicle constituents comprise a monopalmitoyl glycerol surfactant, a hydrophobic substance in the form of cholesterol and a dicetyl phosphate amphiphile. These specific compounds have been shown by the inventors to be particularly suited to the method of the invention.

Preferably, the surfactant, hydrophobic substance and amphiphile are provided in a 5:4:1 molar ratio respectively. This ratio has been shown to work particularly well in the method of the invention.

The NISVs may incorporate a substance that facilitates the transport of fats, fatty acids and lipids across membranes in vivo (such vesicles termed hereafter 'bilosomes'), as also described in PCT/GB96/01861. Thus, preferably a bile salt is provided in the vesicle components and/or when dissolving a pharmaceutical agent in a pharmaceutically-acceptable carrier. The inventors have shown that, advantageously, bilosome delivery has no detectable toxicity in gut tissue and, furthermore, oral delivery of antibiotics in bilosomes has provided a significant survival advantage in two murine models of bacterial disease caused by *B. pseudomallei* and *F. tularensis* respectively.

Preferably, the bile salt is sodium deoxycholate, for example sodium deoxycholate in PBS.

For applications where cell or tissue targeted is warranted, it is preferable that the vesicle components further comprise a ligand recognised by an in vivo receptor-mediated transport mechanism.

The term ligand refers to a substance that can bind to, and/or form a complex with, a biomolecule such as a protein receptor, for example a host cell receptor. Association of the ligand with the vesicles produced by the method of the invention i.e. via incorporation by entrapment within and/or bound to the vesicles during formation of a pharmaceutical-vesicle, can facilitate transportation of the pharmaceutical-vesicle across a specific in vivo barrier or enter a specific in vivo niche (e.g. cell type, tissue type or an intracellular environment), for example as a result of a host receptor-mediated transport mechanism.

In the instance of targeted delivery to the brain, preferably, the ligand is glucosamine and/or transferrin or any variant or fragment thereof.

The term 'variant' as used through the description with respect to a protein may refer to a sequence of amino acids which differ from the wild-type or base sequence from which they are derived, but wherein the variant retains the desired properties of the wild-type or base sequence. For example, a variant derived from transferrin would retain a desired level of ligand structure/function relative to the original transferrin protein, and thus be considered a structural/functional variant. As understood by the skilled person, amino acid substitutions can be 'conservative' i.e. replacing an amino acid with another amino acid with similar properties; or 'non-conservative' i.e. replacing with another amino acid with different properties. As further understood by the skilled person, suitable variants are preferably at least 70% identical, for example at least 75% identical, at least 80% identical, at least 85% identical, at least 90% identical and preferably at least 95% identical compared to the wild-type or base sequence.

The term 'fragment' as used through the description with respect to a protein may refer to any amino acid portion of the wild-type or base sequence, typically wherein the fragment retains the desired properties (e.g. structural, functional) of the wild-type or base sequence. For example, a protein fragment may be a sequence of 5-10 amino acids of the wild-type or base sequence of a protein which encodes a particular epitope, and thus be considered to be an epitope fragment.

The inventors have shown that NISVs modified with glucosamine (to form gNISVs) and/or transferrin (to form tNISVs) (such vesicles termed hereafter termed 'brainsomes') are advantageously adapted to enhance their delivery across the BBB. For example, these glucosamine- and transferrin-modified NISVs have been successfully loaded with the anti-VEEV monoclonal antibody 1A3B-7, in particular the humanised version Hu1A3B-7. Furthermore, antibody-loaded gNISVs have been delivered by intravenous injection to Balb/c mice and the antibody cargo has been detected by immunohistochemistry in brain tissue, peaking at 90 minutes post-injection. The benefit of such modification has been demonstrated by encapsulation of VEEV Hu1A3B-7 monoclonal antibody in NISVs and gNISVs significantly increasing survival in an aerosol model of VEEV compared to free (un-encapsulated) monoclonal antibody (mAb). Survival advantages with encapsulation are associated with decreased viral load in the lung and brain.

Preferably, the glucosamine is palmitoylated glucosamine. Palmitic acid is covalently linked to the glucosamine, enhancing the hydrophobicity of the glucosamine and therefore its ability to insert into the vesicle's bilayer. This form (i.e. variant) of glucosamine is particularly suited to forming gNISVs, as palmitoylated glucosamine can be included in the vesicle formulation by dissolution in the organic phase used in automated protocols. Preferably, the transferrin is thiolated using Traut's reagent, which reacts with the primary amine groups to add a sulfhydryl group. A portion of the cholesterol is replaced by cholesterol-PEG-malemide such that a covalent bond forms between the thiolated ligand and the modified cholesterol. This arrangement enables cell- and/or tissue-targeting ligands to attach to the vesicles. Any ratio of cholesterol to cholesterol-PEG-malemide is envisaged but in particular 4:1 is preferred. Other cell- and/or tissue-targeting ligands can be attached to the vesicle in a similar manner and therefore target the resultant vesicles to other anatomical niches.

Preferably, the pharmaceutical agent-carrier mixture and vesicle components are provided in a respective ratio of 3:1. The inventors have shown this ratio to be particularly suited to the present invention, in particular for vesicles adapted to cross the BBB.

Preferably, the method steps of the invention are performed on a NanoAssemblr® for the preparation of modified vesicles such as gNISVs and tNISVs.

The inventors have shown that the ability to automate and rapidly scale up production of NISV and these variants (bilosomes; brainsomes) has been successfully demonstrated in the commercial-off-the-shelf NanoAssemblr® equipment. Both gNISVs and tNISVs have been generated using the NanoAssemblr® which allows for automation and rapid scale-up of formulations. Furthermore the utility of the NanoAssemblr® to rapidly produce, for example, brainsomes loaded with a range of antivirals (e.g. interferons such as IFN-α2β) highlights nanovesicles as a versatile and attractive drug delivery technology. Additionally, work has been undertaken to successfully scale up and automate the production of brainsomes and bilosomes in the Nanoassemblr®, with characterisation of the batches generated in terms of size and loading.

The pharmaceutical-vesicle formulation can be frozen and lyophilised prior to storage and/or distribution. In this case, preferably a cryoprotectant is added prior to freezing and lyophilisation, for example adding sucrose at 100 mM concentration. The subsequent storage of freeze-dried batches and demonstration of performance following re-hydration has been achieved.

Preferably, the pharmaceutical agent is an antibacterial agent and/or an antiviral agent.

The inventors have successfully shown that biphasic NISV and bilosome formulations were shown to maintain antimicrobial activity in MIC and MBC assays. In each of the assays undertaken by the inventors, bilosome-formulated antibiotics exerted as much antimicrobial activity as unformulated antibiotics, indicating that the process of formulation had not adversely affected the antibiotic being tested. Furthermore, the data reported shows that the bilosome delivery of antibiotics not only provides a significant survival advantage, but also reduces the serious side effect of weight loss associated with repeated antibiotic dosing and infection.

Freeze-dried biphasic NISV and bilosome antibiotic formulations were also assessed for their toxicity in vivo. Encapsulation of antibiotics was seen to be beneficial, in particular by alleviating antibiotic-induced weight loss and protecting from minor organ pathologies. In particular, the results demonstrated that bilosomes had no adverse effects on the murine microbiome. Furthermore, gross pathology data suggested that NISVs and bilosomes can, for example, protect against tissue damage caused by doxycycline. Thus, the NISV and bilosome formulations generated by the method of the invention are well-tolerated and have beneficial properties to counteract the side-effects of repeated, daily dosing with antibiotics.

The antibacterial agent may be selected from the group of antibiotics including β-lactams (e.g. penicillins such as amoxicillin and flucloxacillin; cephalosporins such as cephalexin), aminoglycosides (e.g. streptomycin, kanamycin), chloramphenicol, glycopeptides (e.g. vancomycin), quinolones (e.g. fluoroquinolones such as ciprofloxacin, levofloxacin), oxazolidinones (e.g. linezolid, tedizolid), sulphonamides (e.g. sulfadiazine), tetracyclines (e.g. tetracycline, doxycycline, oxytetracycline), macrolides (e.g. erythromycin, clarithromycin), ansamycins (e.g. geldanamycin, rifamycin), streptomycins (e.g. pristinamycin IA) and lipopeptides (e.g. daptomycin).

Preferably, the antibacterial agent is selected from a group comprising fluoroquinolones and tetracyclines.

Further preferably, the antibacterial agent is selected from a group comprising levofloxacin, ciprofloxacin and doxycycline.

The NISV and bilosome formulation technology has been adapted to successfully entrap at least 3 antibiotics (doxycycline, levofloxacin, ciprofloxacin) in NISVs and bilosomes. The mixture of components (monopalmitoyl glycerol, dicetyl phosphate and cholesterol) is heated rapidly, the chosen antibiotic(s) added and then processed to form the antibiotic-vesicle formulation. Bilosome formulations are prepared by adding bile salts, post-heating stage, at the same time as the antibiotic solution. Formulations with an antibiotic concentration may be 1-100 mg/ml.

Advantageously, the formulations generated are stable and retain antimicrobial activity in vitro and in vivo. For example, characterisation has identified that encapsulation of levofloxacin into NISVs significantly increased survival of *F. tularensis*-infected galleria (a suitable invertebrate infection model). Further in vivo data suggests that vesicle formulations can enhance therapy efficacy, with both the bilosome-levofloxacin and bilosome-doxycycline formulations increasing survival rate and time, compared to free antibiotic in a mouse model of melioidosis. Similar preliminary findings have been shown in an *F. tularensis* model of infection. The inventors have shown that NISVs and bilosomes protect against antibiotic-induced weight loss, for example following administration of ciprofloxacin or levofloxacin. Furthermore, encapsulation of levofloxacin in orally-delivered bilosomes increased accumulation in the liver by two-fold, thus maintaining antibiotic concentrations in this key organ for longer, with positive therapeutic implications.

Preferably, the antibacterial agent is at a concentration of 30 mg/ml. Following continuous development of the process, an antibiotic starting concentration of 30 mg/ml was found to work particularly effectively. Such concentration was achieved by adding antibiotic at a concentration of 30 mg/ml to the pharmaceutically-acceptable carrier, which in turn was added to the vesicle components and the formulation mixture processed. After optionally quantifying the concentration, for example by HPLC, the pharmaceutical-vesicle formulation was resuspended in a volume and concentration of antibiotic in a pharmaceutically-acceptable carrier to give approximately equal antibiotic concentrations inside and outside the vesicles.

The antiviral agent may be selected from the group of antivirals including inhibitors of viral penetration and uncoating, DNA polymerase inhibitors (e.g. acyclovir), mRNA inhibitors (e.g. ribavirin, carbodine), release inhibitors (e.g. neuraminidase inhibitors) and immunomodulators (e.g. interferons).

Preferably, the antiviral agent is selected from a group comprising IFN-γ, IFN-α, carbodine, DZ-13 (Xie et al. Regulatory roles of c-jun in H5N1 influenza virus replication and host inflammation. Biochimica et Biophysica Acta. 1842(2014), 2479-88) and an antiviral antibody or any variant or fragment thereof.

Advantageously, the brainsomes developed by the inventors have been shown to be capable of entrapping large antibodies (including VEEV Hu1A3B-7) and/or a cytokine (e.g. IFNα2β). Furthermore, gNISVs have been shown to enhance delivery of pharmaceutical agents (e.g. IgG Ab) in vivo to the brain compared to free antibody.

Preferably, the antiviral antibody is Hu1A3B-7 VEEV mAb or any variant or fragment thereof.

The Applicants have shown that NISV and gNISV delivery of Hu1A3B-7 VEEV mAb is advantageous compared to free mAb. Both platforms reduce viral load in the lung, and increase survival and reduce morbidity. Significantly, the gNISV platform reduces viral load in the brain.

The invention also provides a pharmaceutical-vesicle formulation prepared according to the first aspect.

According to a second aspect, the invention provides a pharmaceutical-vesicle formulation comprising: a) a vesicle comprising monopalmitoyl glycerol, cholesterol and dicetyl phosphate; b) a pharmaceutical agent; and c) a pharmaceutically-acceptable carrier.

Preferably, the monopalmitoyl glycerol, cholesterol and dicetyl phosphate are present in a 5:4:1 molar ratio respectively.

Preferably, the pharmaceutical-vesicle formulation further comprises a ligand recognised by an in vivo receptor-mediated transport mechanism.

Preferably, the ligand is glucosamine and/or transferrin or any variant or fragment thereof.

Preferably, the vesicle component of the pharmaceutical-vesicle formulation is of a size of 50-4000 nm. For vesicles with an entrapped antibiotic, the vesicle component is preferably 2700-3400 nm. For vesicles modified as brainsomes (e.g. brainsomes with an entrapped antibody), the size is preferably 100-600 nm.

Preferably, the pharmaceutical agent is an antibacterial agent and/or an antiviral agent.

Preferably, the antibacterial agent is selected from a group comprising fluoroquinolones and tetracyclines.

Preferably, the antibacterial agent is selected from a group comprising levofloxacin, ciprofloxacin and doxycycline.

Preferably, the antibacterial agent is present at concentration of 30 mg/ml.

Preferably, the antiviral agent is selected from a group comprising IFN-γ, IFN-α, carbodine, DZ-13 and an antiviral antibody or any variant or fragment thereof.

Preferably, the antiviral antibody is Hu1A3B-7 VEEV mAb or any variant or fragment thereof.

According to a third aspect, the invention provides a pharmaceutical kit comprising the pharmaceutical-vesicle formulation according to the second aspect.

According to a fourth aspect, the invention provides a pharmaceutical-vesicle formulation according to the second aspect, or a pharmaceutical kit according to the third aspect, for use as a medicament.

Preferably, the invention provides a pharmaceutical-vesicle formulation according to the second aspect, or a pharmaceutical kit according to the third aspect, for use as a medicament for the prevention or treatment of infection in an animal.

It is envisaged that the pharmaceutical-vesicle formulation of the invention could be administered to an animal via any route of administration e.g. parenteral delivery via intramuscular (into muscle), subcutaneous (under the skin), intra-dermal (into skin), intra-peritoneal (into the peritoneum body cavity), intravenous (into a vein), intra-nasal (via the nose) or inhalational administration. However, it is preferable, in particular for bilosomes, that the pharmaceutical-vesicle formulation is administered to the animal via an oral route. Surprisingly, the pharmaceutical-vesicle formulation of the invention has shown to augment the benefit of an already bioavailable pharmaceutical agent, including: protecting against antibiotic-induced weight loss in animals; providing for improved target tissue deposition and concentration over time; providing immunomodulatory effects; and conferring a lack of toxicity in the gut, in particular against the gut microbiome.

Preferably, the animal is a human.

Preferably, the invention provides a pharmaceutical-vesicle formulation according to the second aspect, or the pharmaceutical kit according to the third aspect, for use in the prevention or treatment of infection by *Burkholderia pseudomallei*, *Francisella tularensis* or VEEV.

The invention also provides for use of a NanoAssemblr® to prepare a pharmaceutical-vesicle formulation according to the first aspect.

Any feature in one aspect of the invention may be applied to any other aspects of the invention, in any appropriate combination. In particular, the method aspects may be applied to the pharmaceutical-vesicle formulation aspects, the pharmaceutical kit aspects and/or the use aspects and vice versa. The method of the invention extends to a pharmaceutical-vesicle formulation, pharmaceutical kit, and uses substantially as herein described, with reference to the Examples.

In all aspects, the invention may comprise, consist essentially of, or consist of any feature or combination of features.

The present invention will now be described, with reference to the following non-limiting examples and Figures in which:

BRIEF DESCRIPTION OF THE FIGURES

FIG. 3 shows graphs of repeat dose tolerability studies for biphasic NISV and bilosome formulations of antibiotic:body weight changes;

FIG. 13 shows a graph of the effect of bilosome-levofloxacin compared to free levofloxacin in an aerosol model of *F. tularensis*;

FIG. 16 shows a graph of survival in mice in an aerosol model of VEEV following treatment with different Hu1A3B-7 VEEV mAb.

DETAILED DESCRIPTION

Figure 1:
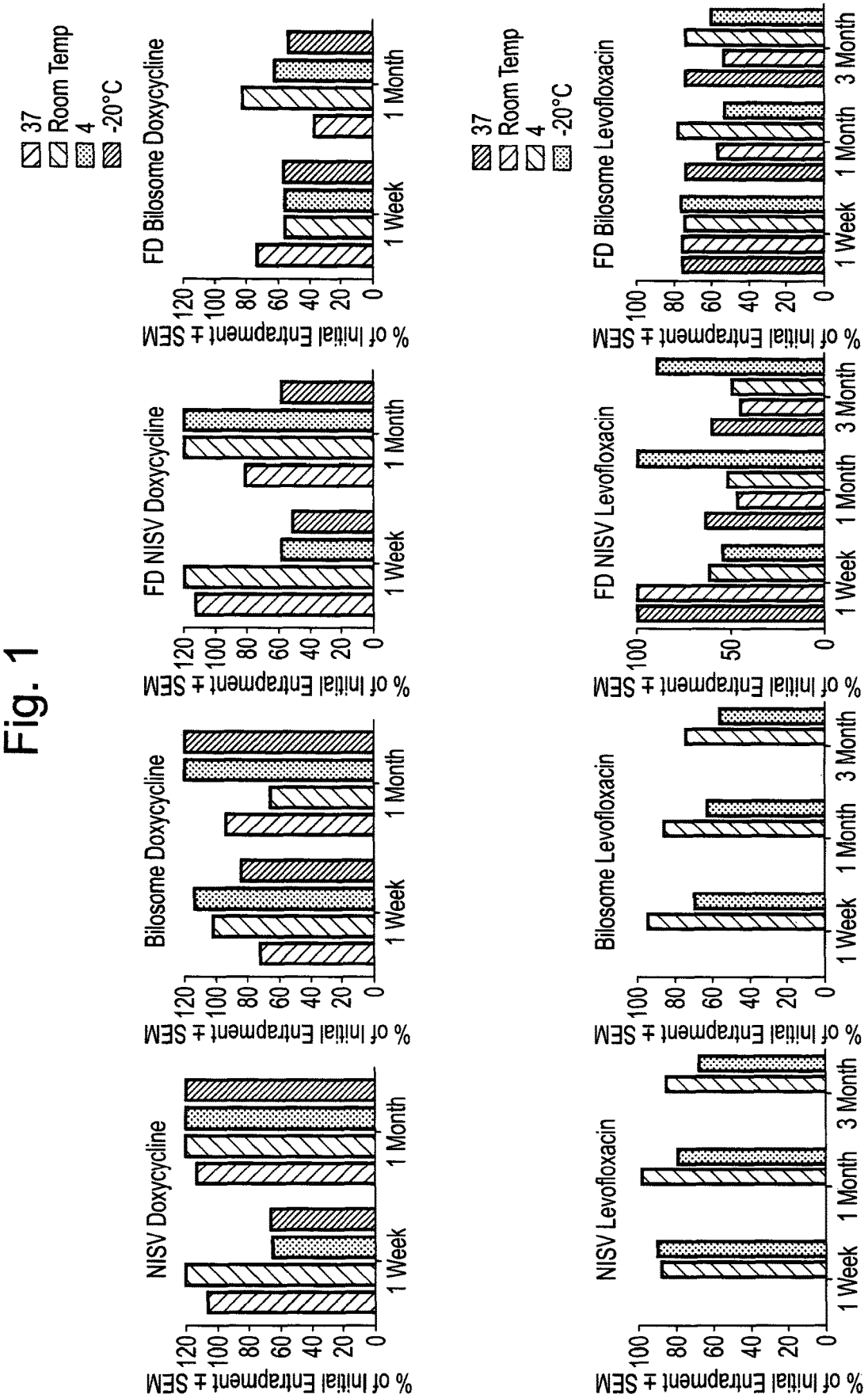
FIG. 1 shows graphs demonstrating the stability of biphasic formulations when stored at a range of temperatures in liquid or freeze-dried format.

The method of the invention provides a method for the preparation of a pharmaceutical-vesicle formulation, the method comprising the steps of: a) heating vesicle components comprising monopalmitoyl glycerol, cholesterol and dicetyl phosphate at a temperature in the range of 50° C. to 150° C.; b) dissolving a pharmaceutical agent in a pharmaceutically-acceptable carrier and heating the resultant pharmaceutical agent-carrier mixture at a range of 30-99° C.; c) adding the pharmaceutical agent-carrier mixture to the vesicle components to provide a formulation mixture; and d) processing the formulation mixture to form a pharmaceutical-vesicle formulation, whereby the pharmaceutical agent and carrier is entrapped within a plurality of vesicles; wherein the pharmaceutical-vesicle formulation is reconstituted in a known quantity of the pharmaceutical agent dissolved in a pharmaceutically-acceptable carrier to provide a biphasic pharmaceutical-vesicle formulation.

Various studies have been carried out to demonstrate, in particular, that the method of the invention provides a delivery system, in particular an oral delivery system, which improves the delivery and efficacy of orally-availably pharmaceutical agents, including orally-available antibiotics. Furthermore, the method provides a delivery system with an unexpected and highly significant benefit in protection against pharmaceutical side effects, for example antibiotic-induced weight loss. In particular, the inventors have shown efficacy of the present invention against *B. pseudomallei, F. tularensis* and VEEV.

Material and Methods

Antibiotics

The antibiotics levofloxacin ≥98.0% (HPLC), doxycycline hyclate ≥98.0% (HPLC) and ciprofloxacin (Sigma-Aldrich) were obtained in dry powder form and used in all studies. For making the bilosome formulations and dosing as unformulated drugs, the antibiotics were suspended in PBS at pre-determined concentrations.

VEEV Monoclonal Antibody Synthesis

Humanised anti-VEEV monoclonal antibody was produced as previously described (S. A. Goodchild, L. M. O'Brien, J. Steven, M. R. Muller, O. J. Lanning, C. H, Logue, R. V. D'Elia, R. J. Phillpotts, S. D. Perkins. A humanised murine monoclonal antibody with broad serogroup specificity protects mice from challenge with Venezuelan equine encephalitis virus. Antiviral Res., 90(2011), 1-8). Briefly, CHO DG44 cells transfected with vector expressing Hu1A3B-7 were cultured in IMDM media supplemented with 10% (v/v) FBS, 1% antimycotic, 25 mg Gentamycin, 1 mM sodium pyruvate, 2 mM glutamine, 1% (v/v) pen/strep, 1% (v/v) non-essential and 1% (v/v) essential amino acids (Gibco) and 10 mM methotrexate (Sigma). Humanised antibody was purified using protein A affinity chromatography using Prosep-A (Millipore) and dialysed into PBS.

Bacteria

The clinical isolate *Burkholderia pseudomallei* K96423 was used for in vitro and in vivo studies. Bacteria were grown in Luria broth at 37° C. on a rotary platform for aerosol challenges and enumerated on L-Agar plates.

*F. tularensis* strain LVS was derived from a vaccine ampoule stored at −20° C. in DSTL's culture collection. Bacteria were cultured overnight at 37° C. on supplemented blood cysteine glucose agar (BCGA), harvested into PBS and diluted to obtain an $OD_{600}$ of between 0.15-0.20 ($1 \times 10^9$ CFU/ml). Bacterial numbers for challenge were determined on agar following serial dilution (1:10) of samples.

Viral Preparations

Tissue culture: The L929 (murine fibroblast) and Vero (simian kidney) cell lines (European Collection of Animal Cell Cultures, UK) were propagated by standard methods using the recommended culture media. For experimental purposes, cells were maintained in Leibovitz L-15 media supplemented with 2% (v/v) foetal calf serum, 2 mM l-glutamine, 50 U/ml penicillin and 50 µg/ml streptomycin (L15MM). Media and supplements were all supplied by Sigma-Aldrich (UK).

Stocks: To prepare virulent virus stocks of VEEV strain TrD, suckling mice were infected intracerebrally with ~10³ pfu virus. Infected brains were harvested at 24 hours, prepared as 10% tissue suspensions in L15MM and clarified by centrifugation at 10,000×g for 15 min. The titre was determined by plaque formation under a carboxymethyl cellulose overlay in Vero cells.

Titration of virus: The titre of virus was determined by plaque formation under a 1.5% (w/v) carboxymethyl cellulose overlay in Vero cells. Briefly, cells were seeded into 24-well plates (1×10⁵ cells well) and incubated overnight. Media was removed and the cells overlaid with 100 µl of virus diluted in L15MM. After an incubation of 30 min at room-temperature, 1 ml of double-strength L15MM diluted in 3% (w/v) carboxymethyl cellulose was carefully added to each well. Cells were incubated for 72 hrs, fixed with 10% (v/v) formal saline overnight and then stained with 0.1% (w/v) crystal violet. The plaques were counted and the amount of virus was calculated.

Preparation of Monophasic and Biphasic NISV and Bilosome Formulations

Briefly, 1-monopalmitoyl glycerol, cholesterol and dicetyl phosphate in a 5:4:1 molar ratio were combined and heated to 130° C. For the preparation of NISVs, the relevant antibiotic at 30 mg/ml in PBS was added. For bilosomes, the relevant antibiotic at 30 mg/ml with sodium deoxycholate in 0.025 M carbonate buffer was added. Antibiotics were pre-warmed to 60° C. prior to addition to the vesicle constituents. Preparations were subsequently vortexed vigorously for 2 min. Antibiotics were either entrapped as vesicles were formed or after by 5 cycles of freeze-thawing. Non-entrapped antibiotic was removed through centrifugation and the pelleted vesicles re-suspended in the appropriate buffer for monophasic preparation, or the appropriate buffer containing an amount of the appropriate antibiotic at a concentration equivalent to that entrapped within the vesicle to give biphasic preparations (i.e. 50/50 entrapped:free preparation).

NISVs were made by melting 24.8 mg monopalmitoyl glycerol, 8.2 mg dicetylphosphate, and 23.2 mg cholesterol at 130° C., adding 5 ml of warmed PBS and vortexing for 2 minutes. Sonicated vesicles were made by mixing the same vesicle components in 5 ml PBS and heated to 90° C. for 60 minutes and after which were sonicated using a probe sonicator for 4 minutes at 20% maximum capacity. To ensure sterility, all vesicles samples were irradiated using an X225 irradiator at 2.2 Gy per minute until a final dosage of 10 Gy.

N-Palmitoyl Glucosamine (NPG) Synthesis 86.3 mg of glucosamine was dissolved in 93 µl of triethanolamine and 15 ml of dimethylsulphoxide. This mixture was then added to 283 mg of palmitic acid N-hydroxysuccinimide and dissolved in 4 ml of chloroform. The solution was stirred for 48 hours at room temperature in the dark. The palmitoylated-glucosamine was precipitated out by chilling the mix and adding ice-cold water. The mix was then applied to a vacuum filter to separate the precipitate. Separate water, chloroform and ethanol washes were applied to the palmitoylated-glucosamine before drying at 40° C. for 48 hours.

Human Holo-Transferrin Thiolation

Human holo-transferrin was modified with a thiol by mixing transferrin with a 10-fold molar excess of Traut's reagent at 25° C. for 1 hour. Excess Traut's reagent was removed using a Vivaspin 6 column with a 5 kDa molecular weight cut-off.

Vesicle preparation using microfluidics Vesicles were prepared using the NanoAssemblr™ benchtop (Precision Nanosytems) with a 300 µm staggered herringbone micromixer chip held at a temperature of 60° C. The vesicle components; palmitin, cholesterol and dicetyl-phosphate were solubilised in menthol in 5:4:1 ratio with a total concentration of 5.62 mg/ml and heated to 60° C. Antibodies (either Rabbit IgG, mAb Hu1A3B-7 or Human IgG-FITC) were solubilised in PBS at 2 mg/ml. The aqueous and solvent streams were mixed at a ratio of 3:1, with a combined flow rate of 12 ml/min. Drug encapsulation and vesicle formulation occurs simultaneously within the microfluidic chip. The methanol and unentrapped drug were removed using a Vivaspin20 (Sartorious) spin column with a 300 kDa molecular weight cut off. Concentration of entrapped antibody was determined using standard Bradford's assay. gNISV were prepared in the same manner with the addition of 6.4 mg palmitoylated glucosamine to the vesicle components dissolved in methanol. tNISV were synthesised by including PEG-Maleimide in the NISV mix. Following removal of the methanol and unentrapped cargo the vesicles were incubated with the thiolated transferrin for 1 hour at 25° C. Excess transferrin was then removed using a Vivaspin 20 column with a 100 kDa molecular weight cut off.

Freeze Drying for Vesicle Formulations

Sucrose was added to NISV preparations to a concentration of 100 mM. Preparations were placed at –80° C. at 24 hours prior to being lyophilised in a Christ Epsilon 2-4LD Freeze Dryer and dried at –40° C. for 48 hours with a condenser temperature of –70° C.

Biophysical Characterisation of Bilosomes

Large batches of bilosome preparations were formulated and aliquoted for lyophilisation and storage. Aliquots were recovered as required and resuspended in reverse osmosis water, followed by vigorous agitation. Vesicle size and zeta-potentials were determined using a Malvern Zeta-sizer (Zetasizer 30000HS, Malvern Instruments Ltd., UK). Vesicles were pelleted by centrifugation and HPLC used to determine entrapped antibiotic content.

HPLC Methodologies

HPLC analysis was carried out on an Agilent1290 Infinity Series HPLC, using a C18 column (150 mm×4.6 mm, 5p) maintained at 50° C. The mobile phase for antibiotics (doxycycline, levofloxacin and ciprofloxacin) consisted of 0.02M $Na_2HPO_4$, pH2 with $H_3PO_4$ and either acetonitrile or methanol.

Stability Studies

Large batches of each NISV and bilosome preparations were formulated and aliquots placed at –20° C., 4° C., room temperature and 37° C. either as liquid formulation or freeze-dried preparations. Aliquots were recovered at the various time-points and the freeze-dried preparations re-suspended in reverse osmosis water followed vigorous agitation. Vesicle size and zeta-potentials were determined using a Malvern Zeta-sizer (Zetasizer 30000HS, Malvern Instruments Ltd., UK). Vesicles were pelleted by centrifugation and HPLC used to determine entrapped drug content.

PK/PD Studies

Freeze-dried preparations of NISV and bilosome formulated antibiotic (50-100 mg/kg) were resuspended in reverse osmosis water and administered to animals by the intraperitoneal route or by gavage. Other groups of mice received the identical concentration of antibiotic as a solution. In initial experiments blood was obtained from superficial venesection at time points up to 24 hours. In subsequent experiments mice were sacrificed by terminal anaesthesia, blood collected from the heart and lung, liver and spleen harvested. Each tissue was weighed and 4× volume of saline added before homogenization. Samples were de-proteinated and passed through a 0.2 μm PFTE filter.

Minimum Inhibitory Concentrations (MICs)

MICs for antibiotic formulations were determined for *B. pseudomallei* strain K96243 and *F. tularensis* SchuS4 using the broth micro dilution method in accordance with the Clinical Laboratory Standards Institute (CLSI) guidelines. Assays were performed in 96 well micro-titre plates in Iso-sensitest broth (BSAC) or Mueller Hinton broth (CLSI), or broth suitable for pathogen requirements, with antibiotic concentrations in the range of 64 mg/L to 0.03 mg/L, and bacteria at a final concentration of approximately $5\times10^5$ CFU/mL. Following incubation at 37° C. for 24 h the optical density (OD) of the plates was read in an automated plate reader at a wavelength of 590 nm. MICs were determined as the concentration that inhibited >80% of bacterial growth.

Minimum Bactericidal Concentrations (MBCs)

MBCs for antibiotic formulations were determined by plating 100 μL aliquots of the MIC dilutions showing no visible growth onto L-agar plates or BCGA plates in triplicate and incubating at 37° C. for 48 hours. The MBC was recorded as the lowest concentration of antibiotic that killed 99.9% of the bacteria in the original inoculum.

*Galleria mellonella* Infection

*G. mellonella* caterpillars were stored in the dark. Caterpillars 0.2-0.3 g in weight were employed in all assays. A 10 ml Hamilton syringe was used to inject 10 ml aliquots of the inoculum ($3\times10^6$ CFU/larvae of *F. tularensis* LVS) into the hemocoel of each caterpillar via the last left proleg. After infection, caterpillars were incubated in plastic containers. A 10 ml Hamilton syringe was also used to inject antimicrobial agents (levofloxacin 15 mg/kg) and controls (PBS) 24 hours post infection. Caterpillars were considered dead when the displayed no movement in response to touch.

Microbiome and Toxicology Studies

BALB/c mice were allocated into groups of twelve mice, and treated via the oral route (0.1 ml/day at 10 mg/ml concentration) with PBS, empty bilosomes, empty NISVs, antibiotic, NISV-antibiotic or bilosome-antibiotic on days 1-7. Faecal samples were collected three days prior to treatment, 24 hrs after the final dose (day 8), 14 days later (day 22) and 28 days after the cessation of treatment (day 36). Animal weights and condition were recorded daily. On day 8, half the mice in each group were sacrificed and serum, small intestine and large intestine were collected. Serum samples were stored frozen at −80° C., the large and small intestines were cleaned of contents, rolled into pinwheels and fixed in 10% formalin. The remaining mice were weighed and observed for an additional 28 days before they were sacrificed and serum and tissues harvested as described for the mice sacrificed on day 8.

DNA Extraction and bTEFAP®

Genomic DNA was isolated from faecal samples using the PowerSoil® DNA Isolation Kit (Qiagen) following the manufacturer's instructions. As an alternative to the recommended 250 mg of soil, approximately 200 mg of faecal sample was added to the PowerBeads tube to undergo cell lysis. Purified DNA was eluted from the spin filter using 50 uL of solution C6 and stored at −20° C. until PCR amplification.

The 16S universal Eubacterial primers 515F GTGCCAGCMGCCGCGGTAA and 806R GGACTACHVGGGTWTCTAAT were utilized to evaluate the microbial ecology of each sample on the HiSeq 2500 with methods via the bTEFAP® DNA analysis service. Each sample underwent a single-step 30 cycle PCR using HotStarTaq Plus Master Mix Kit (Qiagen, Valencia, Calif.) were used under the following conditions: 94° C. for 3 minutes, followed by 28 cycles of 94° C. for 30 seconds; 53° C. for 40 seconds and 72° C. for 1 minute; after which a final elongation step at 72° C. for 5 minutes was performed. Following PCR, all amplicon products from different samples were mixed in equal concentrations and purified using Agencourt Ampure beads (Agencourt Bioscience Corporation, MA, USA). Samples were sequenced utilizing the Illumina HiSeq chemistry following manufacturer's protocols.

The Q25 sequence data derived from the sequencing was processed using a proprietary analysis pipeline (www.mrdnalab.com, MR DNA, Shallowater, Tex.). Sequences were depleted of barcodes and primers then short sequences <200 bp were removed, sequences with ambiguous base calls removed, and sequences with homopolymer runs exceeding 6 bp removed. Sequences were then de-noised and chimeras removed. Operational taxonomic units (OTUs) were defined after removal of singleton sequences, clustering at 3% divergence (97% similarity). OTUs were then taxonomically classified using BLASTn against a curated GreenGenes/RDP/NCBI derived database and compiled into each taxonomic level into both "counts" and "percentage" files. Counts files contain the actual number of sequences while the percent files contain the relative (proportion) percentage of sequences within each sample that map to the designated taxonomic classification.

Statistical analysis was performed using a variety of computer packages including XLstat, NCSS 2007, "R" and NCSS 2010. Alpha and beta diversity analysis was conducted as described previously using Qiime (www.qiime.org).

Dendritic Cell Activation

Bone marrow cells were obtained from the femurs of 8-wk-old male BALB/c mice and differentiated into dendritic cells using GM-CSF-enriched complete DMEM (DMEM 10% foetal calf serum, 100 U/ml penicillin, 100 μg/ml streptomycin and 2 mM L-glutamine). This routinely results in 80% CD11c+ cells. BMDCs were then seeded at $1\times10^6$ cells/well on 24-well tissue culture plates in complete RPMI (RPMI 1640 10% foetal calf serum, 100U/ml penicillin, 100 μg/ml streptomycin and 2 mM L-glutamine) and stimulated with LPS (3 μg/ml) or left unstimulated as controls. Cells were simultaneously treated with NISV produced by the melt method, or the sonication method, or left untreated. Cells were harvested 24 hours later and stained with a 1/100 dilution of anti-CD40-APC, anti-CD80-PerCP and anti-CD86-PE-Cy7 before analysis by flow cytometry. Compensation and PMT voltages were set up using single stained controls. Fluorescent minus one (FMO) control was used in order to identify the correct gating strategy and was used in order to produce a negative control.

Animal Infection Studies

Six to eight week old female BALB/c mice (Charles River, UK) were transferred to a high containment Class III rigid isolator, where they were given unlimited access to food and water and allowed to acclimatise for at least 5 days. Mice were allocated to treatment groups (15 per group) and housed in cages of 5. Mice were challenged with 50-100 CFU (10MLD) of *B. pseudomallei* K96243 or *F. tularensis* SchuS4 via the aerosol route in a nose-only exposure system using a computerised delivery platform (Biaera Technologies). A sub-optimal therapy study design was used, in which antibiotic administration was started at 6h post-infection and administered once daily for only 7 days, to test therapeutic efficacy. The antibiotics levofloxacin and doxycycline were delivered daily by the oral route at 50 mg/kg and treatment was continued for 7 days. The treatment groups comprised bilosome-delivered antibiotics or unformulated antibiotics. A subgroup of 5 mice per treatment group was culled at day 3 p.i. to determine bacterial loads in lung, spleen and liver. Mice were challenged with VEEV Trinidad Donkey Strain by aerosol using a Biaeara aerosol device. Mice were checked twice daily and scored for clinical symptoms and mice were weighed daily. Mice reaching a humane end-point, based on a pre-determined set of objective clinical signs, were promptly culled. Survival times were recorded for some mice and others were culled for analysis of tissues at different time points. All procedures and housing complied with the UK Animal (Scientific Procedures) Act (1986).

Titration of Virus in Tissues

The amount of VEEV strain TrD present in mouse tissues (brain, lung, liver and spleen) was determined by titration in Vero cells. Tissues were removed and homogenized in 2 ml L15MM by passing them through a 70 µm nylon cell strainer (BD Falcon). Cell suspension was then diluted serially (1:10) in L15MM. Diluted homogenate (100 µl) was added to wells of a 24-well plate containing confluent monolayers of Vero cells. The cells were incubated for 72 hrs, after which time the monolayers were fixed by the addition of 10% (v/v) formal saline and stained with 0.1% (w/v) crystal violet.

Cytokine Analysis

For cytokine analysis, 200 ml aliquots of cell suspension were centrifuged for 5 min at 2000 rpm. Supernatants were removed for cytokine analysis and stored at −80 C. The levels of cytokine were measured via 23-plexmurine Luminex array (Bio-Rad), used in accordance with the manufacturer's instructions. In addition, a magnetic plate washer (Bio-Rad) was used for wash steps and samples were ultimately fixed using 4% paraformaldehyde in PBS for at least 24 h at 4° C.

Immunohistochemistry

Formalin-fixed Paraffin-embedded (FFPE) tissue samples were used to standardise a protocol to localise the rabbit IgG in the tissue. Tissue sections were deparaffinised and rehydrated using xylene and a graded series of ethanol and water, finishing with TBS. Several methods were used to retrieve the antigen in the 4-micron tissue sections, including enzymatic digestion with PK (DAKO), and High Temperature Antigen Retrieval (HTAR) with pH6.0 and pH 9.0 buffers (DAKO). The best results were obtained with PK pre-treatment. The enzymatic digestion was stopped (3 washes in TBS) and followed by the incubation with a polyclonal goat anti-rabbit IgG Alexa568 labelled antibody (30 min at RT & 1:100 dilution). After 3 TBS washes, slides were mounted using Vectashield antifade hardset mounting media (Vector laboratories) and studied under fluorescent light in a Nikon Ni-SE microscope.

Similarly, tissue sections were used for immunohistochemical detection of rabbit IgG with light microscopy, using the same antigen retrieval method (PK). The dewaxing/rehydration protocol included a step of endogenous peroxidase quench using a solution of hydrogen peroxide in methanol. A polyclonal biotinylated goat anti-rabbit IgG antibody (Pierce)(30 min at RT diluted 1:200) followed by the avidin-biotin peroxidase complex reaction (Pierce). The reaction was developed using NOVARED (Vector). FFPE sections stained with immunohistochemistry for digital image analysis. The mean intensity was calculated using the image analysis software (Nikon Br-NIS). The maximum intensity would be 100.

Statistical Analysis

A variety of statistical analyses were performed using the program SPSS V21.0 (IBM) or Graphpad PRISM V6.0. Graphs have been constructed using Graphpad PRISM V6.0. Survival data were compared using log rank tests. Continuous data were analysed by parametric analysis (ANOVA, T tests, GLM) when conditions were met (QQ plots to assess Gaussian distribution and Levene's/Bartlett tests for unequal variation) or non-parametric tests (Kruskal-Wallis, Mann-Whitney, Moods) where these criteria were not met. In some cases it was possible for parametric criteria to be attained in the use of transformations such as logarithmic transformation. Contingency tables were used for binary data. Multiple testing corrections for familywise error were performed on individual comparisons with analyses. These included Bonferroni's and Dunn's corrections.

Results

Assessment of Encapsulation Efficiency and Stability

Encapsulation efficiency was determined by removing non-entrapped antibiotic by centrifugation and re-suspending the pellet in an appropriate buffer for immediate analysis via HPLC. The value generated represents the amount of antibiotic that was entrapped into the vesicles. Both monophasic and biphasic formulations were tested for stability, as determined by the retention of the antibiotic in each formulation type over time using HPLC for quantification. The zeta potential and size of the NISV and bilosome samples was also measured.

These analyses determined that the biphasic formulations were far superior to the monophasic formulations and so after the first two time points, only the biphasic formulations were continued in the stability assays. The biphasic formulations of both NISVs and bilosomes were tested both as liquid and as freeze-dried preparations and at a range of temperatures (37° C., room temperature, 4° C. and −20° C.). While optimum stability has been demonstrated by biphasic bilosomes stored freeze-dried, all of the biphasic formulations were relatively stable in terms of antibiotic retention, for the time elapsed in the study (3 months). Representative data for biphasic formulations of levofloxacin and doxycycline are shown are shown in FIG. 1 (percentage of initial entrapped antibiotic over time. Biphasic antibiotic formulations were made as previously described and either left as a liquid solution or subsequently freeze dried (FD) Both formulations were left as a variety of different storage temperatures (37° C., room temperature, 4° C. or −20° C.) and assayed at multiple time points post manufacture (1 week, 1 month, 3 months) to determine the level of antibiotic that has remained internalised in the vesicle. FD formulations were rehydrated at each time point for the assay. Data are presented as a percentage of the initial entrapped antibiotic).

To further exemplify the successful adaption of the bilosome formulation technology to entrap the levofloxacin and doxycycline, the total antibiotic delivered by each formulation in mg/ml, together with percentage of this which was entrapped, is recorded in Table 1. For each formulation, more than 50% of the total antibiotic was entrapped. The mean size of bilosomes with antibiotic cargo was in the range 2700-3400 nm with zeta potentials in the range of −30 to −23, where negative values for zeta potential indicate formulation stability.

TABLE 1

Total loading, percentage entrapment and zeta potential of bilosome formulations. The values presented in the table are generated from making bilosomes via the melt method with entrapped concentrations determined via HPLC following removal of free antibiotic. Size and zeta potential measurements were determined by a Malvern Zeta-sizer and data are presented as raw values for 3 independent samples. Means and SEM are highlighted.

| Antibiotics formulations | Total antibiotic in formulation (mg/ml) | Antibiotic entrapped in formulations (mg/ml) | Percentage entrapped (%) | Size | Zeta potential |
|---|---|---|---|---|---|
| Bilosome-levofloxacin | 19.4 | 11.4 | 58.9 | 2846.0 ± 124.42 | −29.667 ± 0.31 |
| Bilosome-deoxycycline | 17.2 | 9.2 | 53.5 | 3329.33 ± 85.62 | −23.33 ± 0.29 |

The stability (determined via Zeta potential) of the bilosome formulations was tested as freeze-dried preparations at a range of temperatures (room temperature, +4° C. and −20° C.) and at a range of time post-manufacture (1 week, 1 month and 3 months) (Table 2). The bilosome zeta potential remained relatively consistent across all time points and all temperatures. There was slight variability in the bilosome doxycycline formulation if kept at room temperature, however all formulations used in these studies were stored at −20° C. and used within a month of manufacture.

TABLE 2

Stability of bilosomes with time and storage conditions, as measured by zeta potential.

| Storage time | Bilosome formulation | | | | | |
|---|---|---|---|---|---|---|
| | Levofloxacin | | | Doxycycline | | |
| | RT | 4° C. | −20° C. | RT | 4° C. | −20° C. |
| Start | −28.1 | | | −19.8 | | |
| | −30.2 | | | −22.6 | | |
| | −32.7 | | | −27.8 | | |
| Mean | −30.22 | N/A | N/A | −23.40 | N/A | N/A |
| SEM | 0.42 | | | | | |
| 1 week | −24.40 | −28.90 | −17.90 | −24.00 | −28.30 | −28.10 |
| | −26.10 | −31.90 | −18.00 | −30.00 | −27.90 | −25.90 |
| | −25.90 | −31.50 | −19.00 | −27.30 | −26.50 | −28.50 |
| Mean | −25.47 | −30.77 | −18.30 | −27.10 | −27.57 | −27.50 |
| SEM | 0.17 | 0.30 | 0.11 | 0.55 | 0.17 | 0.26 |
| 1 month | −24.20 | −26.50 | −29.80 | −16.50 | −26.70 | −22.20 |
| | −26.30 | −30.00 | −30.20 | −18.40 | −28.20 | −22.80 |
| | −28.00 | −31.00 | −32.70 | −18.70 | −30.00 | −26.50 |
| Mean | −26.17 | −29.17 | −30.90 | −17.87 | −28.30 | −23.83 |
| SEM | 0.35 | 0.43 | 0.29 | 0.22 | 0.30 | 0.43 |
| 3 month | −28.90 | −29.90 | −26.00 | −35.30 | −23.40 | −33.60 |
| | −29.40 | −30.90 | −28.50 | −36.40 | −28.10 | −36.40 |
| | −29.20 | −32.60 | −27.90 | −37.00 | −29.00 | −35.00 |
| Mean | −29.17 | −31.13 | −27.47 | −36.23 | −26.83 | −35.00 |
| SEM | 0.05 | 0.25 | 0.24 | 0.16 | 0.55 | 0.26 |

Bilosome antibiotic formulations were made as previously described and subsequently freeze dried (FD). Formulations were left at a variety of different storage temperature (37° C., Room Temperature, 4° C. or −20° C.) and assayed at multiple time points post manufacture (1 week, 1 month and 3 months) to determine the zeta potential of the vesicles. FD formulations were rehydrated at each time point for the assay. Measurements were determined by a Malvern Zeta-sizer and data are presented as raw values (zeta potential) for 3 independent samples per time point and per storage conditions. Means and SEM are highlighted in bold.

The ability to store the freeze-dried vesicles containing antibiotic at room temperature, or even at 37° C., with no reduction in entrapped antibiotic, is a significant benefit of this formulation technology, obviating the need for cold storage.

In Vitro Assessment of Formulations for Minimum Inhibitory Concentrations (MIC) and Minimum Bactericidal Concentrations (MBC)

To rule out the possibility that the formulations of antibiotics in NISVs or bilosomes would adversely affect antimicrobial function, the MIC and MBCs of the formulations were tested in vitro against *F. tularensis* and *B. pseudomallei*. In each of these assays, NISV- and bilosome-formulated antibiotics exerted as much antimicrobial activity as unformulated antibiotics (Table 3), indicating that the process of formulation had not adversely affected the antibiotic cargo.

Figure 2A:
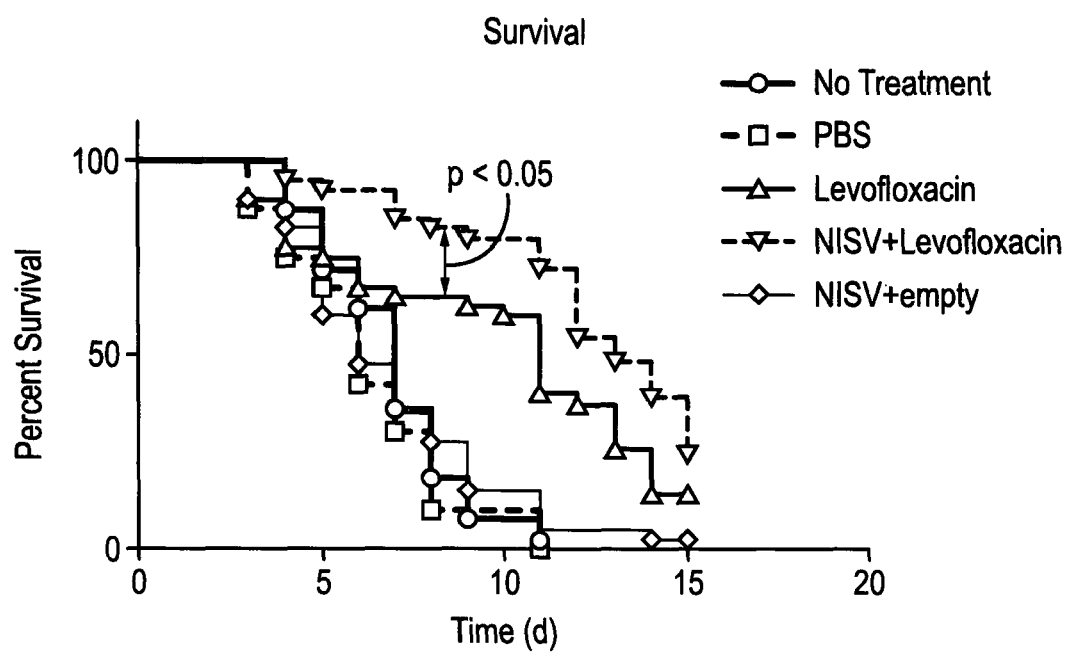
FIG. 2 shows graphs of in vivo assessment of antimicrobial function of levofloxacin formulated in NISVs in the *Galleria mellonella* model.
Figure 2B:
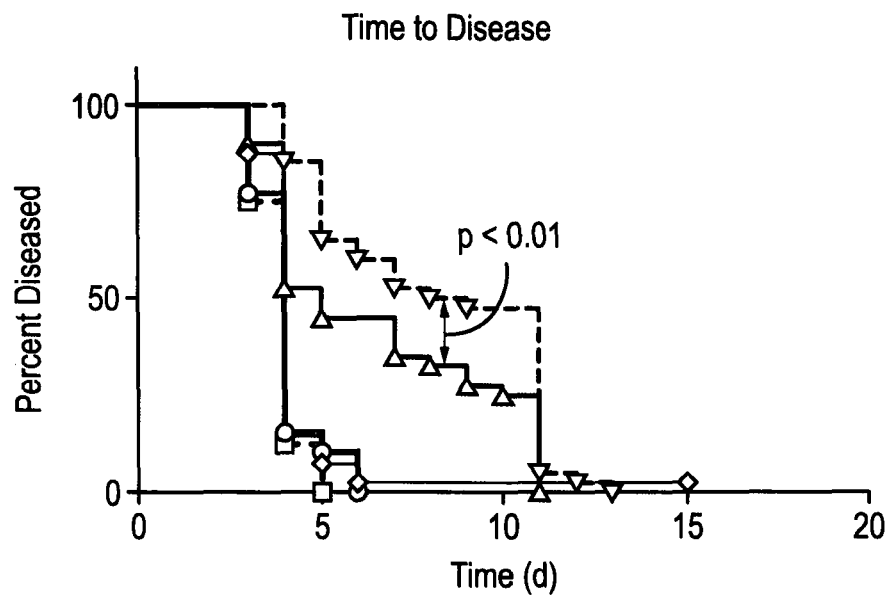

As an adjunct to the in vitro assessment of the formulated antibiotics, the inventors have also carried out some preliminary in vivo screening in a simple model. Using the wax moth larva (*Galleria mellonella*) model, challenged with *F. tularensis* LVS, it was demonstrated that the formulated antibiotics increased both survival and time to disease of *F. tularensis* LVS-infected *G. mellonella* i.e. exerted significantly enhanced antimicrobial activity compared with unformulated antibiotics (FIGS. 2A and 2B; data represented on the graph are Kaplan Meier plots generated from 4 independent experiments with 10 *G. mellonella* per group (total N=40 per group)). Furthermore, the inventors have shown that fluorescently-labelled NISVs are rapidly taken up within 30 minutes into macrophages in vitro, where they continue to accumulate for a further 90 minutes. Using Image Stream technology, the inventors have shown that NISVs are readily visualised in individual cells.

TABLE 3

In vitro assessment of antimicrobial properties of formulated antibiotics by determination of MC and MBC. Values represented on the table are the median value generated from 3 independent experiments with 3 technical repeats in each experiment. MIC is the lowest concentration that inhibits growth i.e. value is recorded when growth is less than 10% of positive control measured by OD. MBC is the lowest concentration that prevents 99.9% of positive control growth i.e. No bacterial colonies present from 10 μl drops on agar plates.

| | Bacteria | | | |
|---|---|---|---|---|
| | *B. pseudomallei* K96243 | | *F. tularensis* SCHU-S4 | |
| Antibiotic Formulations | MIC (μg/ml) | MBC (μg/ml) | MIC (μg/ml) | MBC (μg/ml) |
| Free ciprofloxacin | 2 | 16 | 0.06 | 4 |
| NISV biphasic ciprofloxacin | 2 | 16 | 0.125 | 4 |
| Free levofloxacin | 2 | 32 | 0.06 | 4 |
| NISV biphasic levofloxacin | 2 | 8 | 0.03 | 4 |
| Bilosome biphasic levofloxacin | 4 | 8 | 0.06 | 4 |
| Free doxycycline | 1 | 16 | 0.5 | >64 |
| NISV biphasic doxycycline | 1 | 16 | 1.5 | >64 |
| Bilosome biphasic doxycycline | 1 | 16 | 0.5 | >64 |

In Vivo Screening of Lead NISV and Lead Bilosome Formulations for Tissue Distribution Pharmacokinetic/Pharmacodynamics (PK/PD) Following Parenteral or Oral Dosing NISVs and bilosomes incorporating levofloxacin were selected as the lead formulations for PK/PD analysis in vivo. In a time-course study, female Balb/c mice (n=5 per group) were dosed with NISVs or bilosomes by the intraperitoneal or oral dosing routes respectively, with blood and tissues collected at multiple intervals during a 24 hr period. Blood and tissue samples were processed for analysis of antibiotic concentration by HPLC. The metrics of Cmax (maximum drug concentration during dosing interval), Tmax (time at which the Cm is observed) and area under the curve (AUC i.e. total area under the drug concentration-time course) for levofloxacin which had been formulated in biphasic NISVs or bilosomes and freeze-dried, or for free levofloxacin are shown in Table 4 for blood (panel 1), liver (panel 2) or spleen (panel 3). Levofloxacin dosed orally in bilosomes demonstrated the greatest performance, increasing the AUC value for liver deposition two-fold.

TABLE 4

PK/PD analysis for biphasic formulations of levofloxacin in NISVs and bilosomes. Summary of key PK/PD metrics following dosing via the intraperitoneal or oral route with free, NISV and bilosome levofloxacin formulations in the blood, liver and spleen. Groups of 5 Balb/c mice were dosed and culled at 0.25, 0.5, 1, 2, 4, 8, 16 and 24 hours post treatment. Naïve mice were used as controls. Cmax, Tmax and AUC data were calculated using standard formulae from raw data.

Panel 1

| | | 50 mg/kg dose for all group | | |
|---|---|---|---|---|
| Blood plasma | | Cmax | Tmax | AUC |
| Formulation | Route | μg/ml | Hours | μg/ml/h |
| Levofloxacin | Intraperitoneal | 50.2155 | 0.3 | 122.1861 |
| FD biphasic NISV levofloxacin | Intraperitoneal | 50.5442 | 0.45 | 120.8761 |
| levofloxacin | Oral | 46.07238 | 0.6 | 119.6124 |
| FD biphasic bilosome levofloxacin | Oral | 44.21877 | 0.3 | 116.8437 |

Panel 2

| | | 100 mg/kg dose for all groups | | |
|---|---|---|---|---|
| Liver | | Cmax | Tmax | AUC |
| Formulation | Route | μg/ml | Hours | μg/ml/h |
| Levofloxacin | Intraperitoneal | 2.099737 | 0.25 | 5.73601 |
| FD biphasic NISV levofloxacin | Intraperitoneal | 1.125444 | 0.6 | 5.339507 |
| Levofloxacin | Oral | 1.947519 | 0.25 | 6.588408 |
| FD biphasic bilosome levofloxacin | Oral | 1.698263 | 0.35 | 11.59386 |

Panel 3

| | | 100 mg/kg dose for all groups | | |
|---|---|---|---|---|
| Spleen | | Cmax | Tmax | AUC |
| Formulation | Route | μg/ml | Hours | μg/ml/h |
| Levofloxacin | Intraperitoneal | 1.289808 | 0.25 | 1.092219 |
| FD biphasic NISV levofloxacin | Intraperitoneal | 0.655502 | 0.3 | 1.182148 |
| Levofloxacin | Oral | 0.569373 | 0.35 | 1.552381 |
| FD biphasic bilosome levofloxacin | Oral | 0.699086 | 0.4 | 1.562795 |

Safety/Toxicology Studies on Bilosome Formulations

A study was performed to evaluate the tolerability of ciprofloxacin, levofloxacin and doxycycline formulations given daily for 14 days in Balb/c mice. One hundred and twenty (120) female Balb/c mice were allocated to twelve

(12) groups of ten (10) mice and were treated as shown in methods on days 1-14. Animal weights and condition were recorded daily. No mice died during this study. However, weight changes were noticed between treatment routes and antibiotic formulations (results shown in FIG. 3).

It was shown that ciprofloxacin administered via the I.P or oral route significantly induced weight loss as the experiment progressed (P<0.001). However, encapsulation of ciprofloxacin into NISVs and bilosomes significantly negated this weight losing effect by approximately 25% and 40% respectively (P=0.002). The effect of levofloxacin on overall weight loss via both the I.P and oral routes was minimal with NISV and bilosome encapsulation having no effect (P=0.499 and P=0.616 respectively). A strong indication for doxycycline-based weight loss was observed as the experiment progressed when administered via both routes (P<0.001). Encapsulation in bilosomes did not significantly alter the weight loss but encapsulation of deoxycycline into NISVs had a minor positive effect (P=0.091).

On day 15, half the mice in each group were sacrificed and necropsies performed. The remaining mice were weighed and observed for an additional 7 days before necropsies were performed. No abnormal findings were noted on day 15 or day 22 in groups treated with any ciprofloxacin or levofloxacin antibiotic formulations. Some minor pathological observations were made in the doxycycline-treated groups. On day 15 no abnormal findings were noted in mice receiving doxycycline orally, but mice receiving doxycycline via IP injection had rounded edges on the liver and peritoneal adhesions, involving the peritoneal wall and the intestines (large and small). These findings were consistent in all animals in both IP groups (NISV and PBS).

On day 22, again no abnormal findings were noted in mice receiving doxycycline bilosomes orally. In the group receiving doxycycline in PBS orally, two mice had slightly rounded edges to the lobes of the liver. In the groups treated with doxycycline via the intraperitoneal routes, minor peritoneal adhesions were seen in some of the NISV encapsulated groups, but all mice treated with the PBS-doxycycline formulation showed peritoneal adhesions involving spleen, pancreas, intestines and kidney. Overall, these findings suggest that NISV and bilosome formulations of antibiotics significantly improve tolerability, with tissue protecting effects, for repeated dosing of antibiotics.

A repeat-dose safety/toxicology study was carried out to evaluate the tolerability of the bilosome antibiotic formulations. Groups of 10 mice were dosed daily with 0.1 ml (at a concentration of 1 mg per mouse) of each antibiotic. Bilosome formulations were administered by the oral route. Suitable controls (free antibiotic in PBS) were included for all groups. Mice were weighed daily and data recorded as percentage change from starting weight.

The effects of treatment with different antibiotics, formulated in either saline or bilosomes, were evaluated on weight gain, microbiome composition, small intestine histology and serum serotonin levels. Levofloxacin, doxycycline or ciprofloxacin were given orally for seven days, and half the mice were sacrificed on day 8 to evaluate the immediate impact of treatment. Faecal pellets were collected from mice sacrificed at day 8. The remaining mice were monitored for 28 days after the cessation of treatment, with faecal pellets collected at day 22 and terminal samples collected on day 36.

Figure 4:
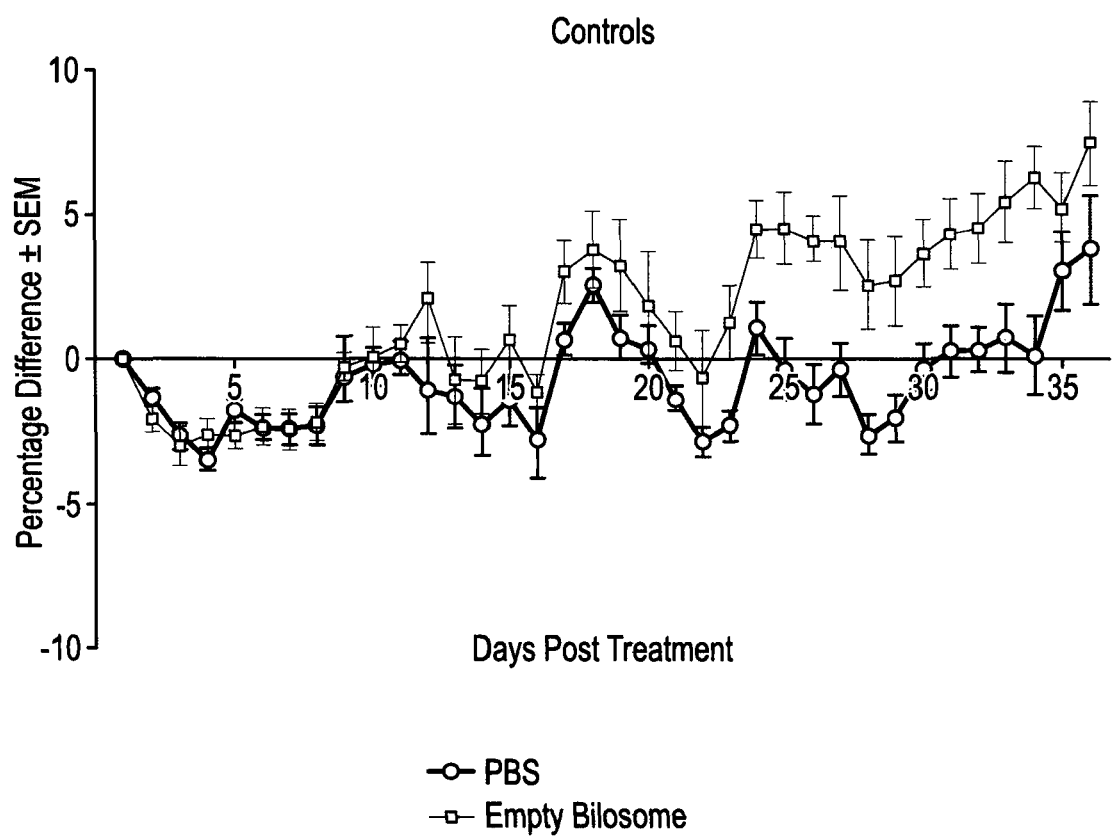
FIG. 4 shows a graph demonstrating weight change in mice control groups for a repeat safety/toxicology study.
Figure 5:
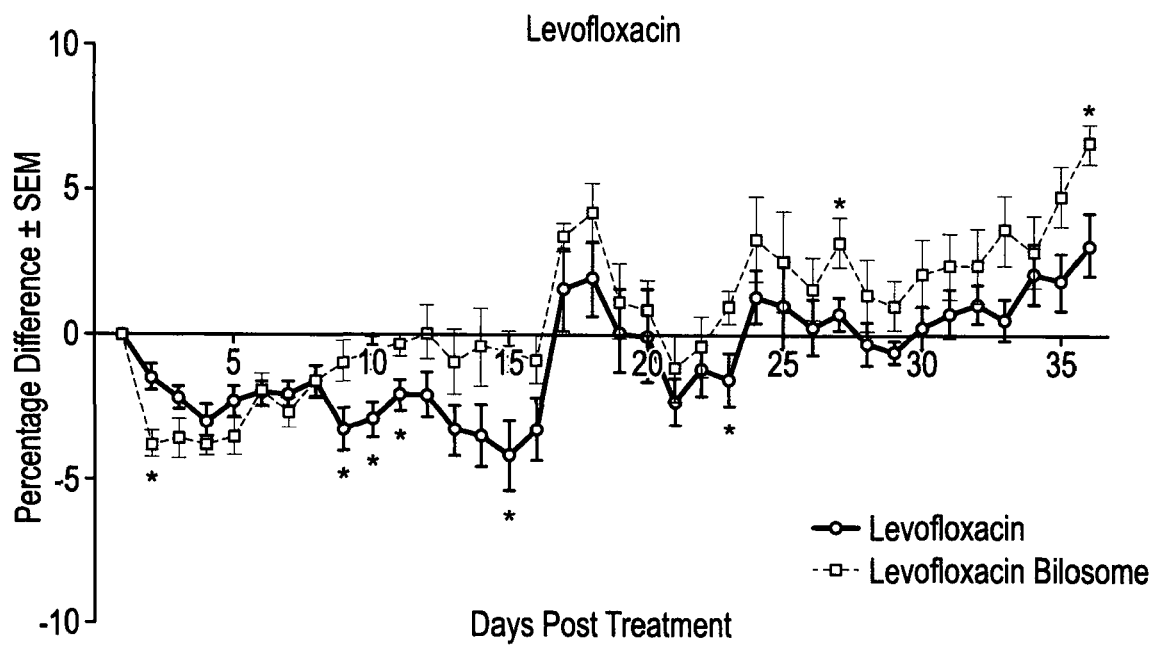
FIG. 5 shows a graph demonstrating weight change in mice following daily dosing with levofloxacin formulations in a repeat safety/toxicology study.
Figure 6:
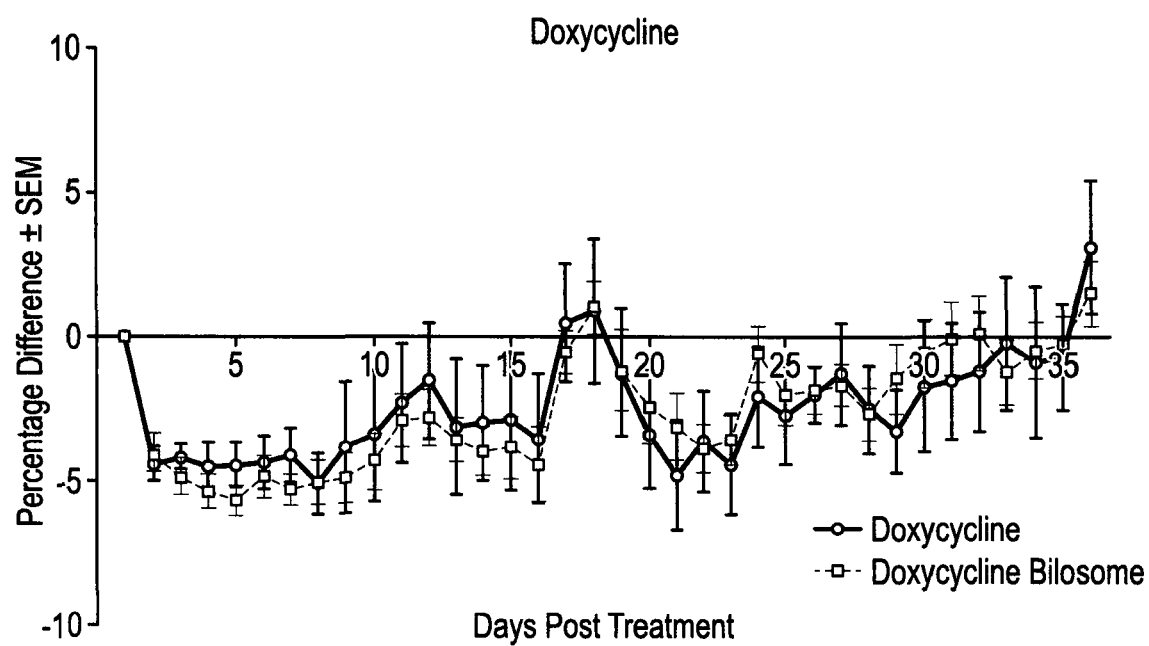
FIG. 6 shows a graph demonstrating weight change in mice following daily dosing with deoxycycline formulations in a repeat safety/toxicology study.
Figure 7:
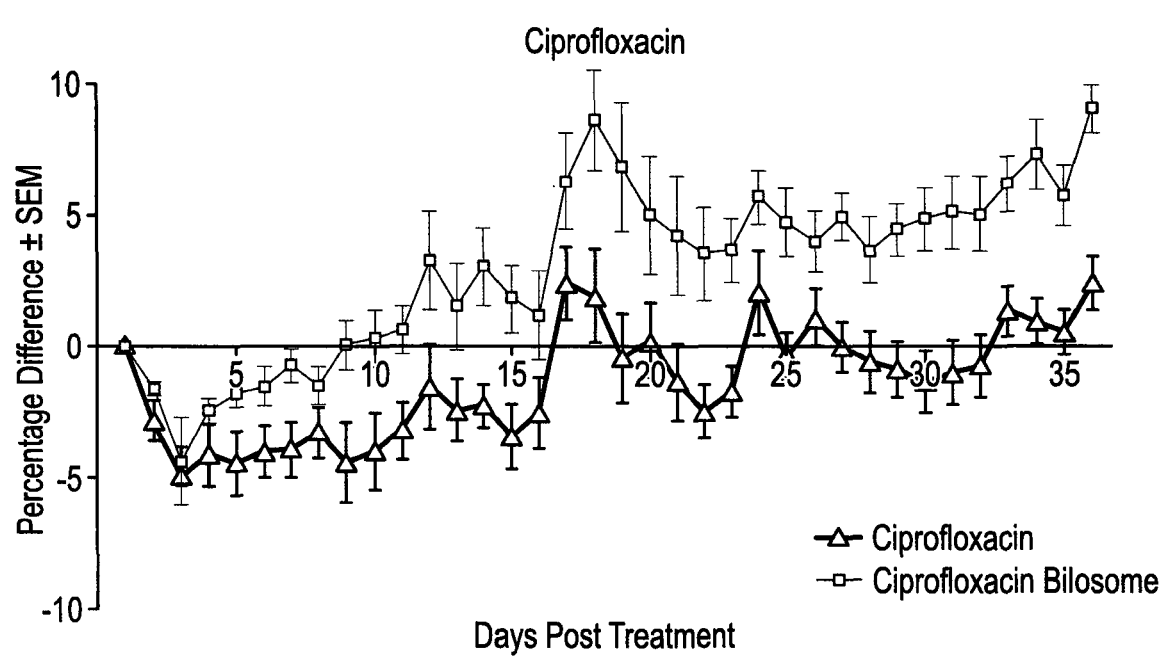
FIG. 7 shows a graph demonstrating weigh change in mice following daily dosing with ciprofloxacin formulations in a repeat safety/toxicology study.

No mortality was noted, small intestine histology was normal in all animals, and there were no statistically significant differences between groups in serum serotonin levels (data not shown). However statistically significant differences in weight gain were noted between treatment groups (FIG. 4 (PBS and empty bilosome control groups); FIG. 5 (levofloxacin formulations); FIG. 6 (deoxycycline formulations); FIG. 7 (ciprofloxacin formulations); percentage daily weight change for each animal and the means for each treatment group were calculated. Error bars represent the standard error for the mean (SEM)).

In the group treated with PBS, mice had a mean weight loss of 0.6% of their starting weight by Day 8, and a mean weight gain of 3.8% on Day 36. The mice treated with empty bilosomes lost an average of 0.3% of their starting weight by Day 8, and had a mean weight gain of 7.5% on Day 36. The mice treated with levofloxacin in PBS lost an average of 3.3% of their starting weight by Day 8, and had a mean weight gain of 3.2% on Day 36. In the group treated with levofloxacin bilosomes, mice had a mean weight loss of 0.9% of their starting weight by Day 8, and a mean weight gain of 6.6% on Day 36. In the group treated with doxycycline in PBS, mice had a mean weight loss of 5.2% of their starting weight by Day 8, and a mean weight gain of 1.7% on Day 36. The mice treated with empty-doxycycline bilosomes lost an average of 0.9% of their starting weight by Day 8, and had a mean weight gain of 1.5% on pay 36. The mice treated with ciprofloxacin in PBS lost an average of 4.4% of their starting weight by Day 8, and had a mean weight gain of 2.4% on Day 36. In the group treated with ciprofloxacin bilosomes, mice had a mean weight gain of 0.1% of their starting weight by Day 8, and a mean weight gain of 9.1% on Day 36.

In particular the bilosome levofloxacin group loss significantly less weight than mice treated with unformulated levofloxacin at days 9, 10, 11, 15, 23, 27 and 36 post treatment (p<0.05). Interestingly therapy ended at day 8 and that is when 3 consecutive days of significant weight difference between groups was observed. No significant difference was seen between bilosome doxycycline and free doxycycline treated groups.

To evaluate the significance of the differences seen in weight gain the Area Under the Curve (AUC) for the percentage weight change for each animal was calculated and the groups compared using a one-way ANOVA test. In this analysis, the data were evaluated to the end of the dosing period on Day 8 and for the animals that were sacrificed on Day 36. In the analysis of the data to Day 8, the ANOVA test indicated that significant differences were seen between groups (p=0.0001), and in the data to Day 36 the ANOVA test also indicated significant differences (p=0.0020). Group-to-group comparisons were performed on the data to evaluate the impact of single variables. Importantly this analysis indicated that there were statistically significant differences between the group treated with ciprofloxacin in PBS and ciprofloxacin bilosomes (p=0.0152). Similar positive trends were seen when comparing levofloxacin in PBS vs levofloxacin bilosomes and PBS vs empty bilosomes.

Microbiome Analysis

To investigate the ability of bilosomes to ameliorate antibiotic-induced weight loss, the microbiome of mice was monitored for 36 days following treatment with free antibiotic or bilosome-encapsulated antibiotic. Mice were administered antibiotic and the microbiome characterised by next generation sequencing. Genus data was categorised into specific phyla to which they belong and percentage abundance for each treatment group was calculated. Data was graphed on area charts/stacked bar charts.

Figure 8:
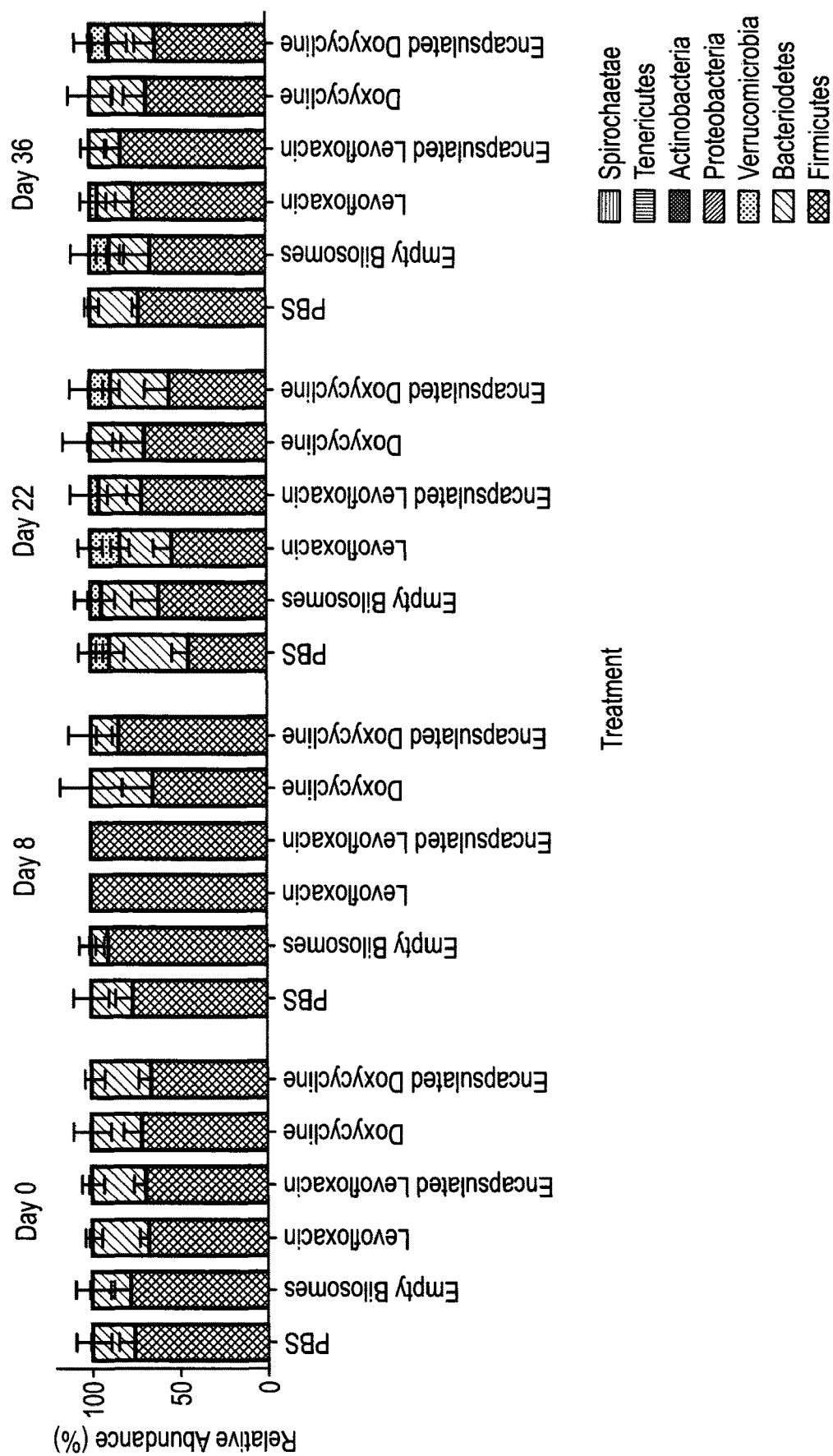
FIG. 8 shows graphs of broad microbiome analysis following treatment with antibiotic formulations.

The results demonstrate that bilosomes had no adverse effects on the microbiome (FIG. 8). In general, the effect of antibiotic treatment was to reduce the Gram-negative bacteriodetes and increase the Gram-positive firmicutes at day 8, with a gradual restoration to pre-treatment ratios by day 36. However, these changes were accompanied by the appearance of small amounts of Verucomicrobia species in bilosome treated groups, which are thought to have beneficial effects in the microbiome.

A total of fifty-nine (59) genera were defined as high frequency (present in at least 75% of specimens). There was some variation in the presence of these 59 genera in the baseline samples, but at least 57 genera were present in all groups. Slight reductions in representation were seen on days 8 and 22, with some recovery by day 36. The content of the doxycycline-bilosome group was substantially lower than all the other groups at all time points. Upon evaluation of the data, it became clear that this was due to a near-complete absence of clostridia sequences in this group, which were present at high levels in all other groups. Most samples in the doxycycline-bilosome group, including all samples on days 8 and 22, were devoid of clostridia, while the few samples that did have clostridia, had 100-1000 fold less clostridia than samples from other groups.

A total of eighty-one (81) genera were defined as low frequency (present in less than 25% of specimens). No more than 15 of these 81 genera were present in any one group at any time point, with most genera being absent from most specimens. In total, these genera accounted for very little of the total microbial complement, however the data suggest that bilosome levofloxacin treated groups had a more diverse microflora for these low frequency genera.

Thus, overall, microbiome analysis demonstrated that the bilosome platform is well tolerated in vivo and may encourage the restoration of bacteriodetes and growth of beneficial bacteria (Verucomicrobia) in the gut following antibiotic disturbance.

Immunomodulatory Properties

Figure 9:
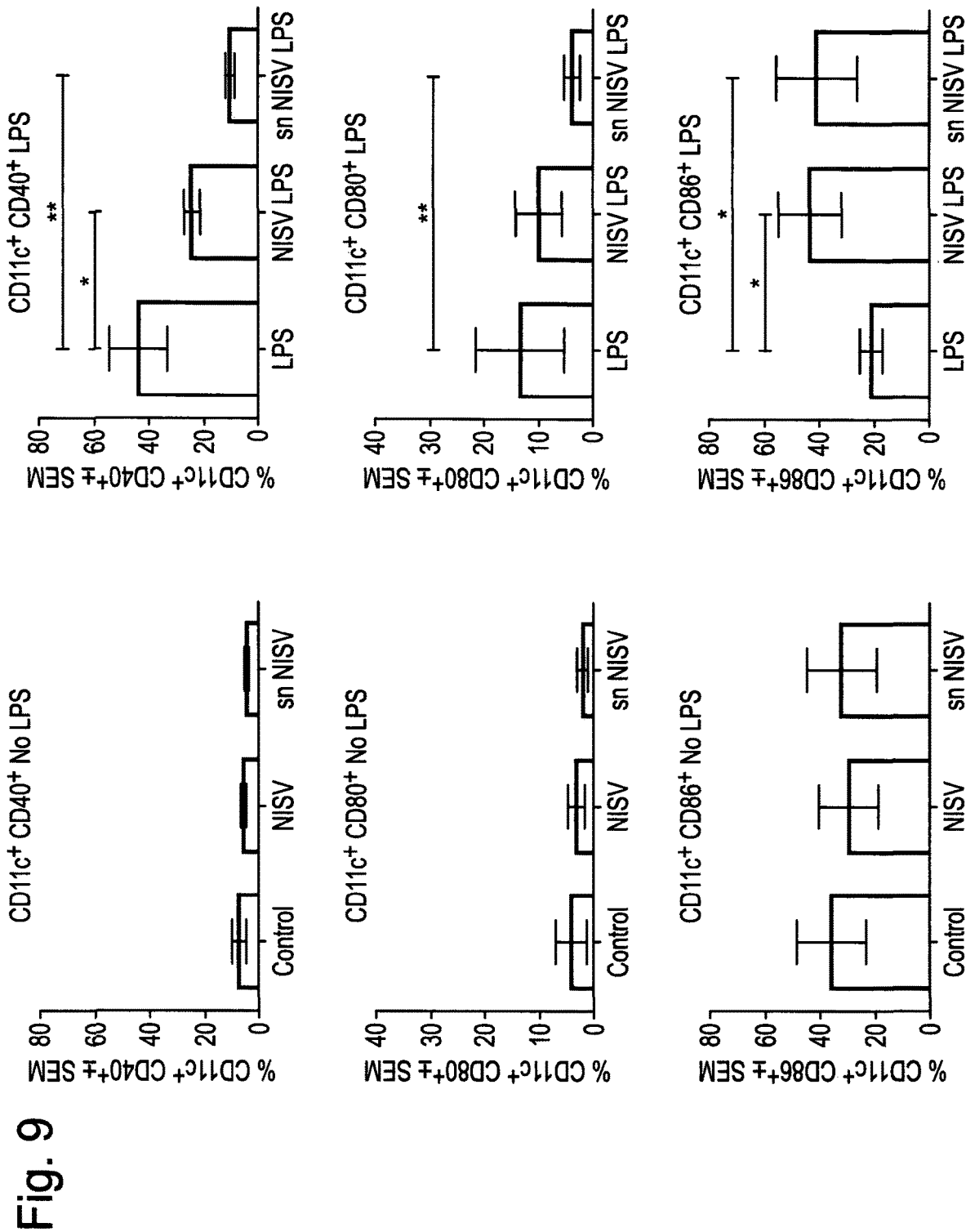
FIG. 9 shows graphs of the modulation of dendritic cell activation in the presence of NISVs.

Bone marrow cells were obtained from the femurs of 8-wk-old male BALB/c mice and differentiated into bone marrow-derived dendritic cells (BMDCs) using GM-CSF-enriched media. This routinely resulted in 80% $CD11c^+$ cells. BMDCs were then seeded at $5 \times 10^5$ cells/well on 96-well microtiter tissue culture plates and stimulated with LPS (3 ug/ml) or left unstimulated as controls. Cells were simultaneously treated with NISV produced by the melt method, or the sonication method (sn NISV), or left untreated. Cells were harvested 24 hrs later and stained with antibodies to CD40, CD80 or CD86 before analysis by flow cytometry. CD40, 80 or 86 levels were not affected in non-LPS stimulated cells treated with either NISV formulation (FIG. 9; $*p<0.05$, $**p<0.01$). However, CD40 and CD80 levels were downregulated in LPS-stimulated cells treated with either NISV formulation (FIG. 9). In contrast, CD86 levels were augmented in LPS-stimulated cells treated with either NISV formulation, which is typical of the maturation of myeloid DCs (FIG. 9).

Figure 10:
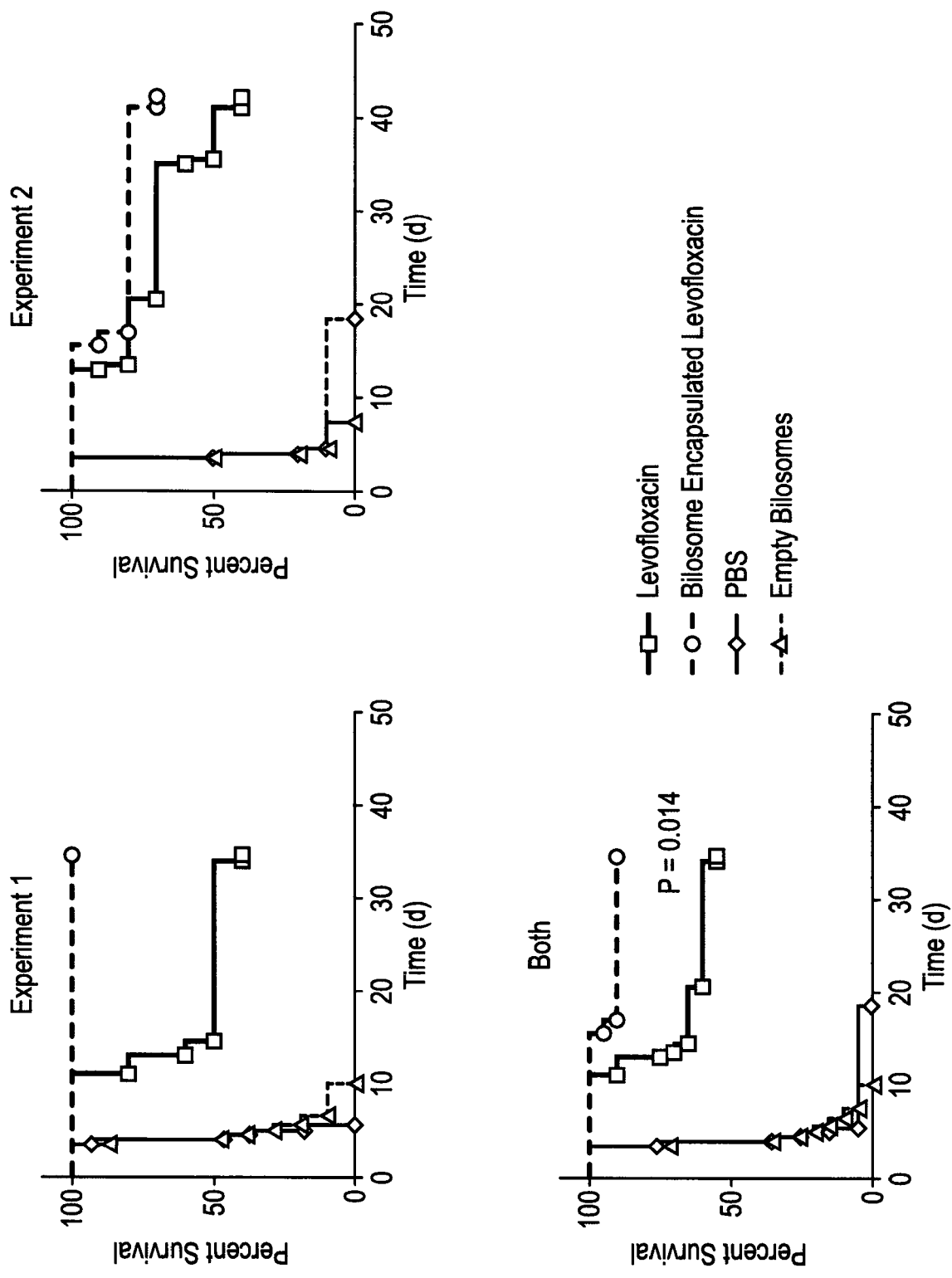
FIG. 10 shows graphs of the effect of bilosome-levofloxacin compared to free levofloxacin in an aerosol model of *B. pseudomallei*.
Figure 11:
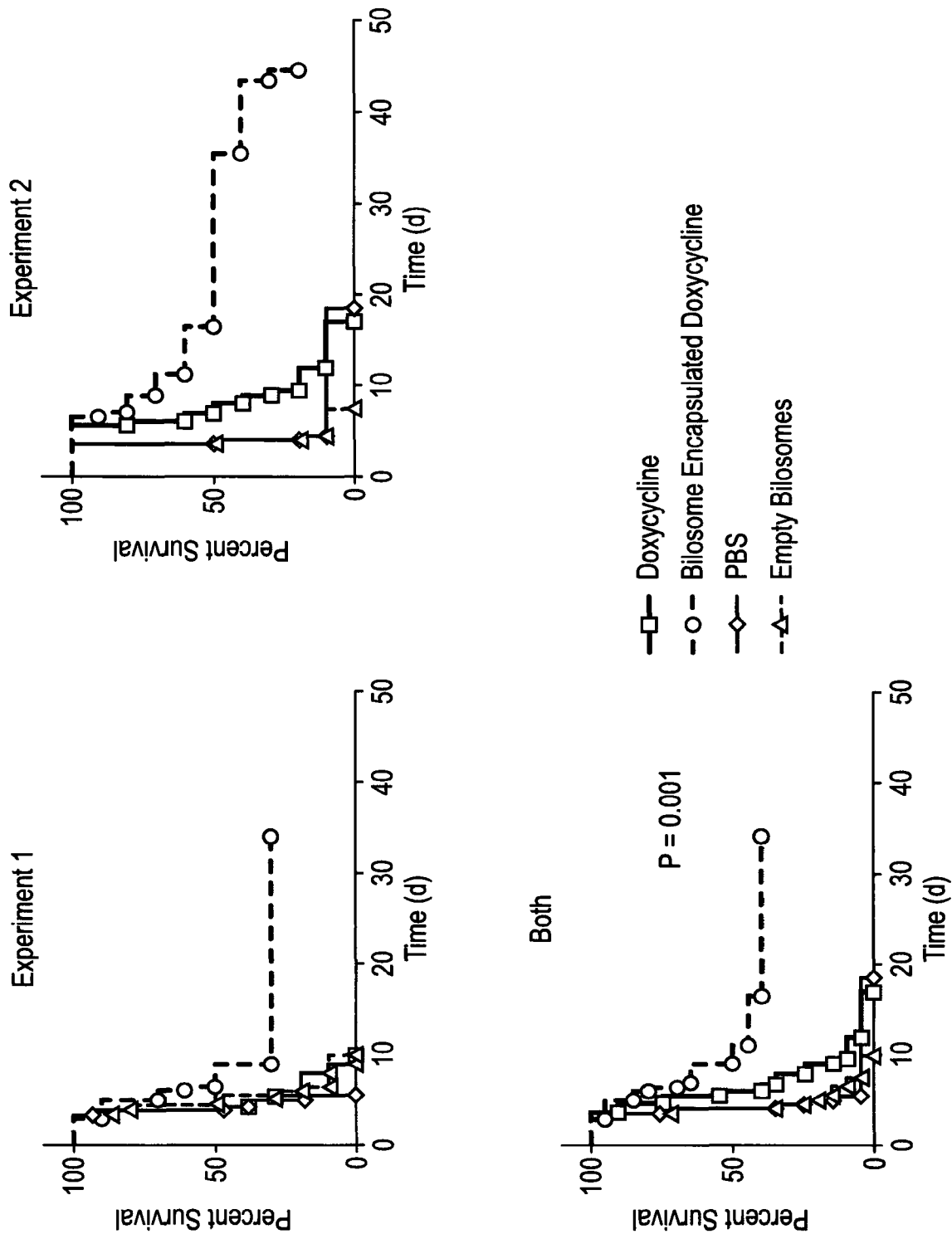
FIG. 11 shows graphs of the effect of bilosome-doxycycline compared to free doxycycline in an aerosol model of *B. pseudomallei*.

In Vivo Assessment of Bilosome Formulations to Treat B. pseudomallei and F. tularensis Infection The efficacy of bilosome formulations of levofloxacin and doxycycline was tested in an aerosol model of melioidosis, using a sub-optimal therapy study design, in which antibiotic administration was started at 6 hours post-infection and administered once daily via the oral route for only 7 days, to test therapeutic efficacy. The treatment groups comprised bilosome-delivered antibiotics or unformulated antibiotics, with control groups receiving PBS or empty bilosomes. This study was repeated twice with exactly the same design, conditions and identical treatment groups, the data were stratified and combined for analysis, to give an overall significant survival advantage for bilosome-encapsulated versus free levofloxacin ($p=0.014$) (FIG. 10) and for bilosome-encapsulated versus free doxycycline ($p<0.001$) (FIG. 11). Data represented on the graphs are Kaplan Meier plots, with 10 mice per group. Both figures show the results of Experiment 1 (top left panel), Experiment 2 (top right panel) and combined stratified data (bottom panel). PBS and empty bilosome treatment groups were included as controls.

Figure 12:
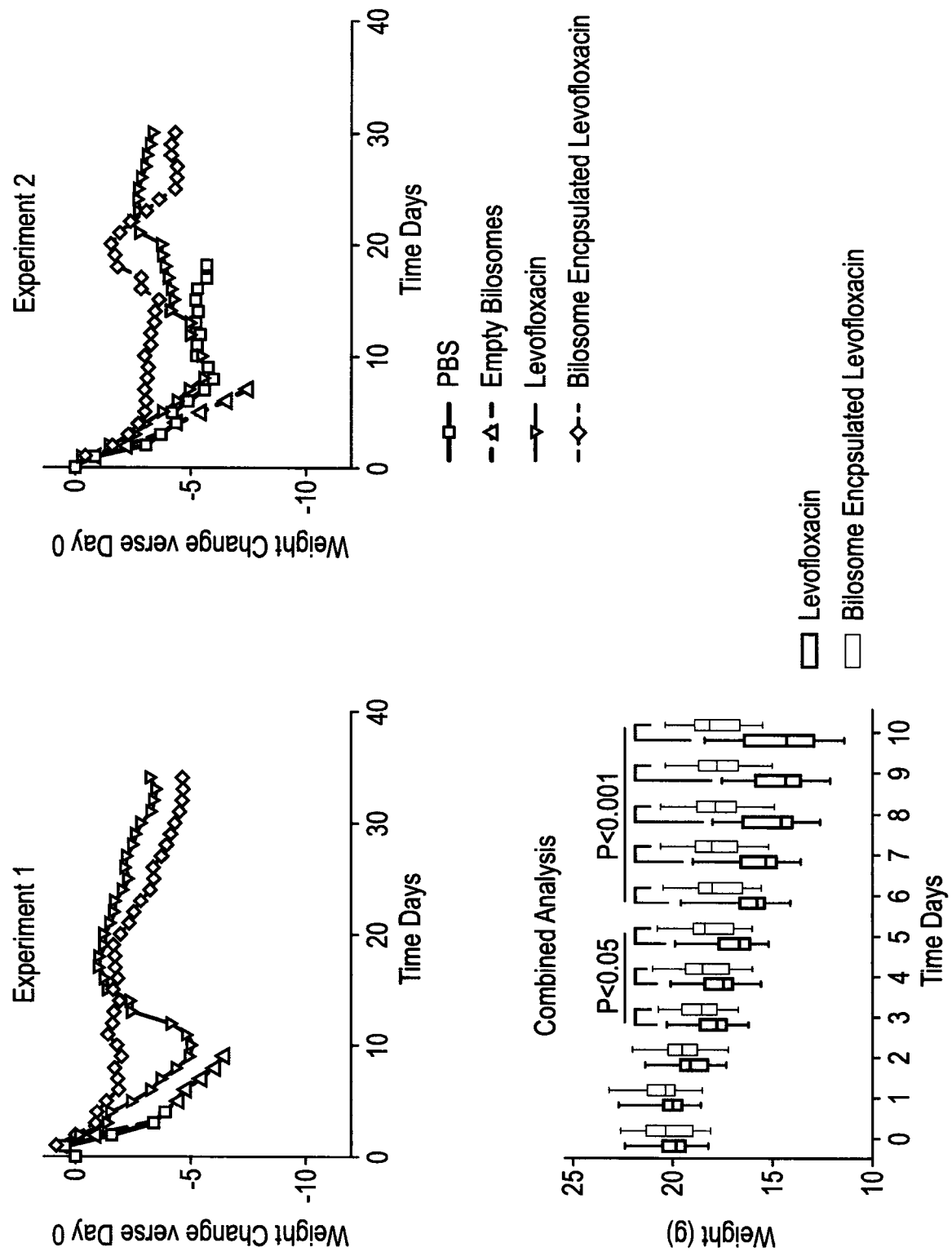
FIG. 12 shows graphs of animal weight data following exposure to an aerosol challenge of *B. pseudomallei* and treatment with bilosome-levofloxacin or free levofloxacin.

In addition to the survival advantage conferred by delivering levofloxacin in bilosomes, over free levofloxacin, bilosome-levofloxacin-treated groups lost significantly less body weight compared to levofloxacin (FIG. 12). Data represented are plots for individual mice (Experiment 1 (top left panel); Experiment 2 (top right panel); and combined data uses box and whisker plots with inter quartile ranges (bottom panel)). PBS and empty bilosome treatment groups were included as controls. In the levofloxacin treatment groups, the protection against antibiotic-induced weight loss in mice receiving the bilosome formulations was very marked, such that the combined data from the bilosome-levofloxacin treated groups gave a highly significant difference in weight loss ($p<0.001$, FIG. 12).

Figures 13, 16:
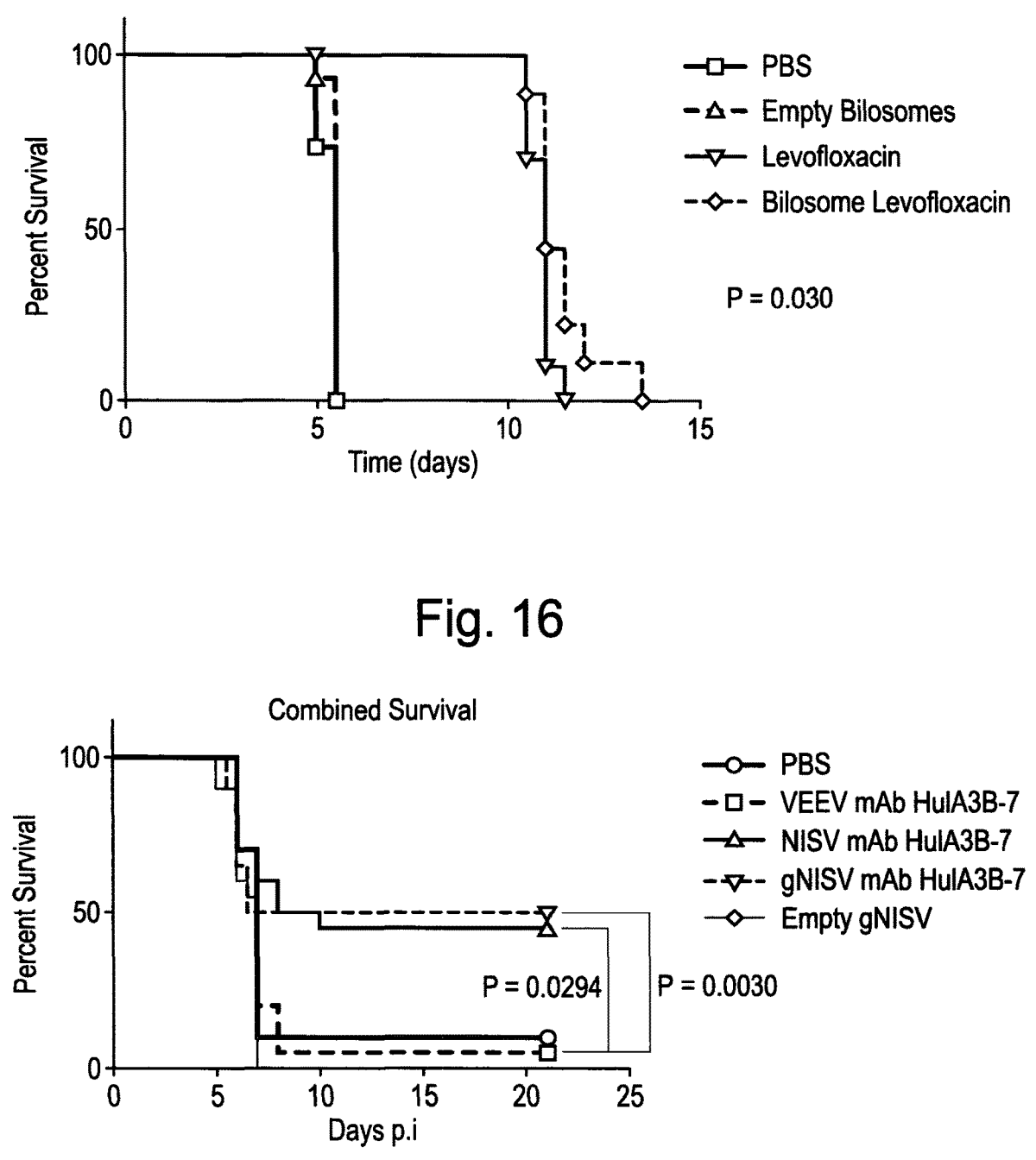

Similarly to B. pseudomallei, Balb/c mice were treated with bilosome-delivered levofloxacin p.i. with F. tularensis. Antibiotic therapy (20 mg/kg) was commenced at 72 hours after exposure to 100 cfu of aerosolised F. tularensis SchuS4 (approximately 20 MLD) and delivered daily for only 3 days to groups of 15 mice. Animals receiving bilosome-delivered levofloxacin by the oral route had a significantly ($p<0.05$) extended time to death, compared with those receiving free levofloxacin (FIG. 13). This result provides further evidence of the advantages of bilosome delivery of antibiotics.

Bacteriological, immunological and blood chemistry analyses show supporting changes between bilosome and free antibiotic-treated groups. At day 3 p.i. with B. pseudomallei, cytokine analysis of lung, spleen and liver tissue samples showed a decrease in pro-inflammatory cytokines in bilosome-levofloxacin treated groups and this correlated with a reduction in ALT and GGT, enzymes associated with liver damage.

Other evidence of beneficial effects of bilosome delivery of antibiotic has been derived from the F. tularensis study in which mice administered bilosome-entrapped levofloxacin had significantly reduced levels of some key inflammatory cytokines, compared to those mice receiving unformulated levofloxacin ($p<0.05$: IL-6 lung, IL-13 spleen, Eotaxin Liver, GM-CSF lung and liver, MIP1b liver). Analysis of cytokine levels in Burkholderia-infected mice has shown similar trends.

Overall, the data indicate that bilosome delivery of antibiotic not only provides a significant survival advantage, but also reduces side effects associated with repeated antibiotic dosing and modulates the immune response to reduce cytokine-induced morbidity that is normally evident in these infections.

Entrapment of a Range of Antivirals in Modified NISVs

In order to develop an effective therapy for the encephalitic viruses (e.g. VEEV), NISVs have been modified to facilitate their passage across the blood brain barrier (BBB). This approach has been achieved by coating with palmitoylated glucosamine, or covalently linking the cholesterol moiety in the NISV formulation to transferrin, to create gNISV and tNISV respectively ('brainsomes'). Palmitoylated glucosamine has been incorporated into gNISV with a view to binding Glut-1 receptors (prevalent in the endothelial tissues of the BBB) in vivo. Similarly, tNISV have been prepared by thiolation of human holo-transferrin to allow it to bind a maleimide modified cholesterol component substituted for a portion (29%) of the normal cholesterol included in NISVs.

To optimize the entrapment of antibodies into NISVs and brainsomes and specifically. as model for the VEEV mAb, we have used non-specific rabbit IgG. This has been successfully entrapped into NISV, gNISV and tNISV at high efficiency (achieving 25-32% entrapment) (Table 5). Using these conditions, VEEV Mab has been incorporated into gNISV with a similarly high efficiency and formulated into tNISV (Table 5). IFNα2β has also been successfully entrapped into NISV with excellent efficiency (43%).

TABLE 5

Physiochemical characterization of NISV variants loaded with antiviral cargo (or surrogate).

| Formulation | Size (nm) | Zeta potential | PDI | Percentage entrapment |
|---|---|---|---|---|
| gNISV IgG | 600 | 17 | 0.6 | 30 |
| tNISV IgG | 316 | 10 | 0.5 | 25 |
| NISV IgG | 300 | 20 | 0.7 | 32 |
| gNISV VEEV | 200 | 13 | 0.4 | 25.9 |
| NISV IFNa2b | 100 | 12 | 0.6 | 43 |

Characterisation of Automated (Scaled-Up) NISV Preparation

Nanovesicle production (brainsomes and bilosomes) has been successfully scaled-up in the NanoAssemblr®, with the aim of achieving a routinely automated and consistent manufacturing process to prepare nanovesicles with selected coatings and of optimized size ranges. NISV, brainsomes and bilosomes have all been successfully made using the NanoAssemblr® (Table 6). Modification of NISVs to provide brainsomes had no significant effect on properties of zeta potential or vesicle size, compared with non-coated NISVs.

TABLE 6

Characterisation of automated (scaled-up) NISV preparations

| Vesicles | Size (z-average nm) | Zeta potential (-mV) | Concentration (mg/ml) |
|---|---|---|---|
| NISV deoxycyline | 175 | 22.7 | 20 |
| NISV levofloxacin | 124 | 20 | 11 |
| Bilosome levofloxacin | 136 | 20 | 13 |

In Vitro and In Vivo Characterisation of NISV Deposition Including BBB-CNS Delivery Assessment Initially, gNISV were stained with Hoechst dye as a model cargo, since the dye is unable to cross the BBB under normal circumstances. Stained gNISV were injected intravenously in the Balb/c mouse and brain tissue removed at 90 minutes. As expected, Hoescht dye alone did not cross the BBB and was not detected in brain. gNISV with encapsulated Hoechst dye crossed the BBB to stain the nuclei of cells, whereas little nuclear staining was detected with unmodified NISV encapsulating Hoechst dye. These data indicate that the gNISV are able to cross the BBB and release their cargo.

Having demonstrated that gNISV can deliver this model cargo, gNISVs have subsequently been used to encapsulate a polyclonal rabbit antibody (MW 150 kDa), with the intention ultimately of encapsulating the humanised anti-VEEV monoclonal IgG, Hu1A3B-7.

Figure 14:
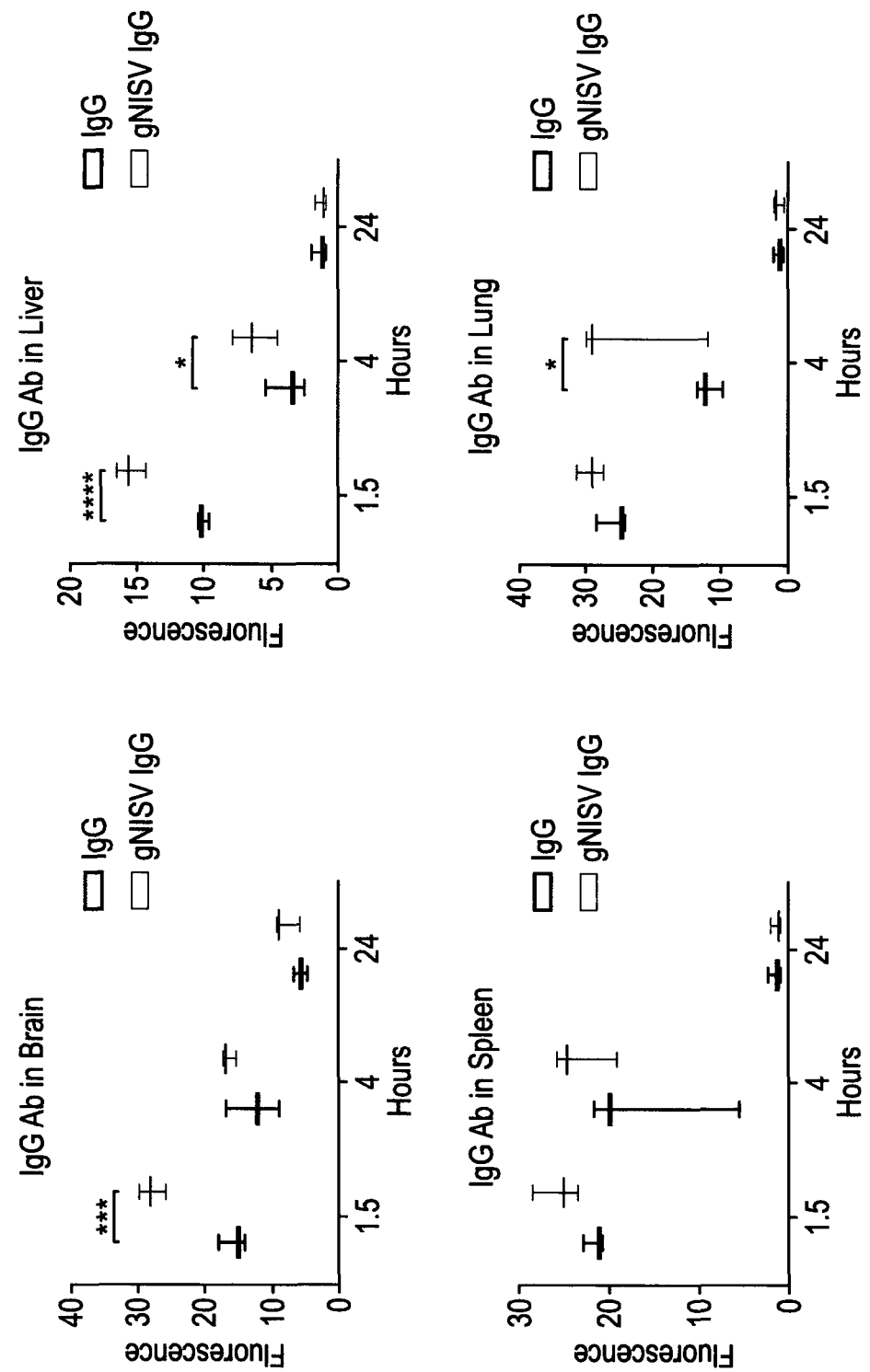
FIG. 14 shows graphs of rabbit IgG antibody deposition in mouse tissues.

Initial studies whereby the rabbit IgG encapsulated in gNISV has been delivered, on a single occasion by intravenous injection to the mouse, have revealed the presence of the antibody in mouse brain at 90 minutes (FIG. 14; tissue slices were fluorescently stained for rabbit IgG and total fluorescence in tissue slice measured with image analysis software. Data represented are means of 3 individual mice per time point and per group. Free IgG antibody was used as a control). Whilst antibody levels in brain had declined by 4 hours, significantly enhanced levels of antibody delivered by gNISV, were present in liver and lung at this timepoint.

The encapsulation of Hu1A3B-7 into gNISV and tNISV has been Walled. Immunohistochemical analysis of mouse brain after intravenous delivery of rabbit IgG in gNISV has demonstrated the presence of the rabbit antibody not only associated with brain vasculature, but also widespread in the brain tissue from these mice, in contrast to brain tissue from mice injected with unformulated rabbit antibody.

Detailed Assessment of Lead NISV Formulation p.i. With Aerosolised VEEV

The VEEV mAb Hu1A3B-7 (S. A. Goodchild, L. M. O'Brien, J. Steven, M. R. Muller, O. J. Lanning, C. H, Logue, R. V. D'Elia, R. J. Phillpotts, S. D. Perkins. A humanised murine monoclonal antibody with broad serogroup specificity protects mice from challenge with Venezuelan equine encephalitis virus. Antiviral Res., 90(2011), 1-8; further disclosed in WO2011036435A1) was the chosen antiviral used during in vivo infection studies. A lethal aerosol model of VEEV infection was used with BALB/c mice exposed to ~300PFU of VEEV Trinidad Donkey strain. This challenge causes clinical signs of infection at approximately 2 days p.i. with time to death between 5-6 days.

It was demonstrated that the process of encapsulation and freeze drying had no detrimental effect on the activity of the mAb, with plaque assays giving similar results for free mAb and NISV and gNISV formulations of the mAb. Empty vesicles controls were shown not to have any anti-viral activity and acted the same as media-only controls (data not shown).

A small scale preliminary study was conducted to test the utility of giving the therapy via the IV route (Table 7). 5 BALB/c mice per group (PBS control, Empty vesicle control, VEEV Hu1A3B-7 mAb, NISV Hu1A3B-7 mAb and gNISV Hu1A3B-7 mAb) were exposed to VEEV via the aerosol route with intravenous treatment given once p.i. at 24 hrs. All mice were culled at day 5 p.i. prior to control mice succumbing to disease. Brain and lung tissues were removed and processed for viral titres. The NISV platform delivered intravenously significantly decreased viral load in the lung and brain (P=0.001 compared to PBS control and P=0.007 compared to free mAb; data not shown).

TABLE 7

Animal study plan for NISV and gNISV mAb intravenous treatment of aerosol VEEV infection.

| Groups | Treatment regimen | Route of therapy | Therapy initiated at PC (hours) | Length of treatment (days) | No. of mice |
|---|---|---|---|---|---|
| 1a | PBS | Intravenous | 24 | 1 | 5 |
| 2a | VEEV mAb Hu1A3B-7 | Intravenous | 24 | 1 | 5 |
| 3a | NISV mAb Hu1A3B-7 | Intravenous | 24 | 1 | 5 |

TABLE 7-continued

Animal study plan for NISV and gNISV mAb intravenous treatment of aerosol VEEV infection.

| Groups | Treatment regimen | Route of therapy | Therapy initiated at PC (hours) | Length of treatment (days) | No. of mice |
|---|---|---|---|---|---|
| 4a | gNISV mAb Hu1A3B-7 | Intravenous | 24 | 1 | 5 |
| 5a | Empty gNISV | Intravenous | 24 | 1 | 5 |

To better fully characterise the differences between NISV platform formulations and free compound, an intraperitoneal treatment model was used (Table 8). This route has previously been shown to be more consistent and suitable for assessing the efficacy of the Hu1A3B-7 mAb.

TABLE 8

Animal study plan for NISV and gNISV mAb intraperitoneal treatment of aerosol VEEV infection.

| Groups | Treatment regimen | Route of therapy | Therapy initiated at PC (hours) | Length of treatment (days) | No. of mice |
|---|---|---|---|---|---|
| 6a + b | PBS | Intraperitoneal | 24 | 1 | 10 |
| 7a + b + c | VEEV mAb Hu1A3B-7 (100 µg in 100 µl) | Intraperitoneal | 24 | 1 | 15 |
| 8a + b + c | NISV mAb Hu1A3B-7 (100 µg in 100 µl) | Intraperitoneal | 24 | 1 | 15 |
| 9a + b + c | gNISV mAb Hu1A3B-7 (100 µg in 100 µl) | Intraperitoneal | 24 | 1 | 15 |
| 10a + b | Empty gNISV (100 µg) | Intraperitoneal | 24 | 1 | 10 |

Identical treatment groups (PBS control, Empty vesicle control, VEEV Hu1A3B-7 mAb, NISV Hu1A3B-7 mAb and gNISV Hu1A3B-7 mAb) were assessed using the aerosol VEEV model, with therapy again given once at 24 hours via the intraperitoneal route. In these studies a total of 15 mice per treatment group were used, with 5 mice being culled for virology analysis at day 5 p.i. and the remaining 10 mice monitored for survival.

Two independent studies of identical design were carried out and showed similar results for all treatment groups. In experiment 1, both the NISV and gNISV entrapped Hu1A3B-7 mAb reduced viral load in the lung compared to PBS treated groups (p<0.001 and P=0.003 respectively). NISV-entrapped mAb was also significantly different from free Hu1A3B-7 mAb in terms of viral titre in the lung (p<0.001). NISV entrapped mAb also performed better in the spleen compared to PBS and free Hu1A3B-7 VEEV mAb (p<0.001 and <0.05 respectively). Importantly the gNISV-encapsulated mAb, specifically designed to target the brain performed significantly better than all other formulations and controls in the brain. This lead to increased survival in the NISV and gNISV treated groups with NISV being significantly better than free Hu1A3B-7 VEEV mAb (p=0.008).

In experiment 2, the gNISV performed better than the PBS control in the lung (p=0.0031) and significantly better in the brain compared to all formulations. The NISV and gNISV formulation performed significantly better than PBS controls in the spleen tissue (p=0.0143 and P<0.001 respectively). Interestingly the free Hu1A3B-7 VEEV mAb also showed a beneficial effect in the spleen indicating that the therapy was efficacious despite the low VEEV-specific active component. In this experiment, gNISV mAb significantly improved survival compared to free Hu1A3B-7 VEEV mAb (p=0.0036) and NISV mAb groups showed a similar trend.

Figure 15:
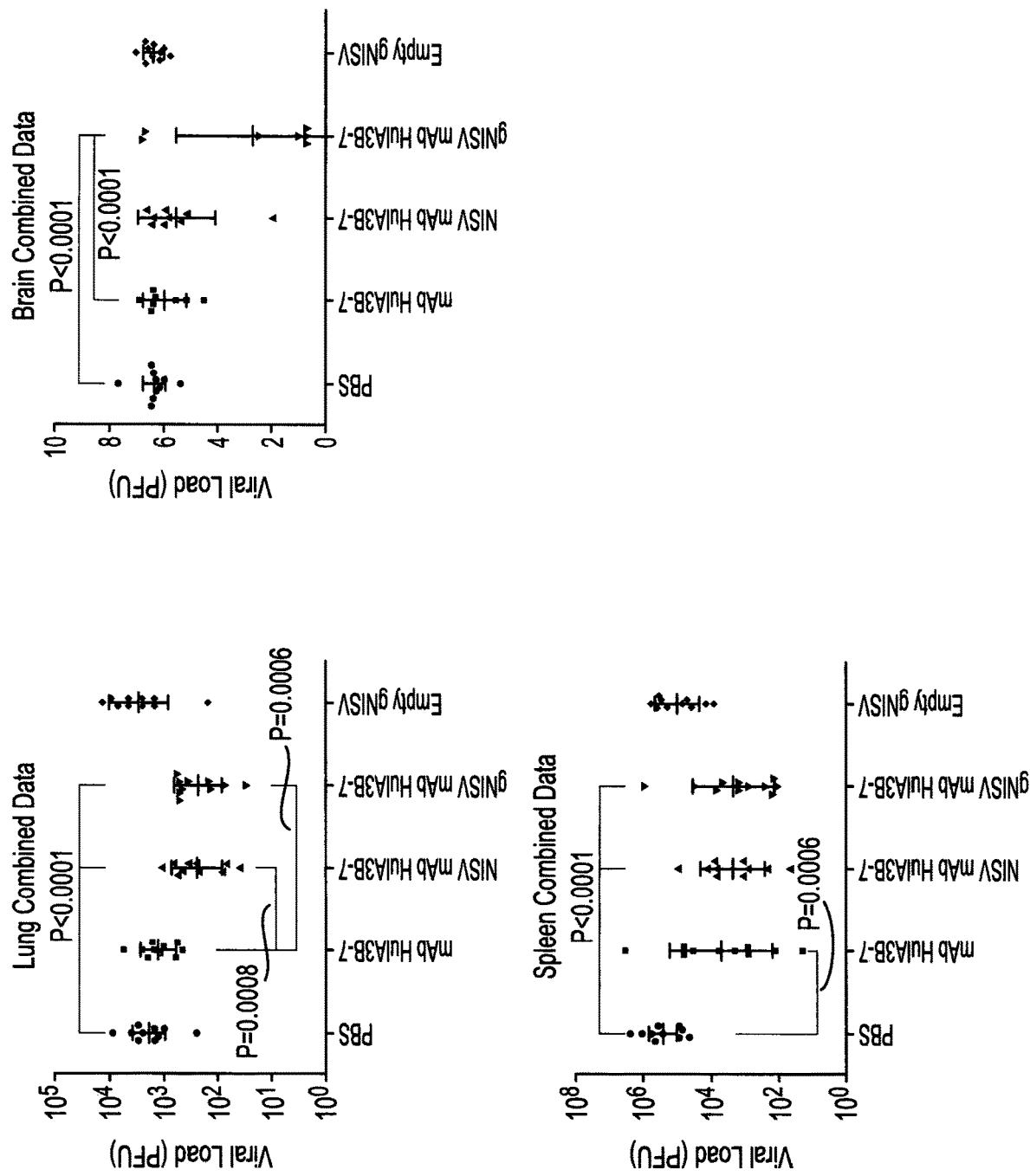
FIG. 15 shows graphs of viral load in mice organs following treatment with different formulations of Hu1A3B-7 VEEV mAb.

When the data from experiments 1 and 2 are combined, the positive effects of free Hu1A3B-7 VEEV mAb are clear, but more importantly the advantages provided by the encapsulated formulations (NISVS and gNISVs) are highlighted. Both the NISV and gNISV mAb formulation significantly reduced viral load in the lung compared to PBS and free Hu1A3B-7 VEEV mAb controls. Furthermore, the gNISV significantly reduced viral load in the brain compared to both controls. Interestingly the spleen data showed that the free Hu1A3B-7 VEEV mAb provided therapeutic benefit by significantly reducing viral load compared to the PBS controls, although the viral load in the spleens of NISV and gNISV mAb groups did not differ significantly from the free Hu1A3B-7 group (FIG. 15; BALB/c mice challenged with aerosolised VEEV. A total of 10 mice per treatment group were culled at day 5 p.i. with viral titre determined in the lung, rain, spleen and liver. P values generated by ANOVA and multiple comparisons).

The limited effect of the free mAb in the lung and brain was most likely due to the level of VEEV-specific active component in the preparation. This however further highlights the advantage of NISV encapsulation, by demonstrating the ability to increase the efficacy of sub-optimal levels of therapeutic compound. This is consistent with the antibiotic data where sub-optimal levels of antibiotic were used to demonstrate the advantage of NISV and bilosome entrapment.

Reference to a Sequence Listing Submitted as a Text File Via Efs-Web

The official copy of the sequence listing is submitted electronically via EFS-Web as an ASCII formatted sequence listing with a file named D1722_sequence listing.TXT, created on Mar. 3, 2021, and having a size of 4.096 kilobytes. The sequence listing contained in this ASCII formatted document is part of the specification and is herein incorporated by reference in its entirety.

Combining the survival data from experiments 1 and 2 shows that both the NISV and gNISV Hu1A3B-7 VEEV mAb formulations performed significantly better that PBS and free Hu1A3B-7 VEEV mAb (p=0.0294 and p=0.0030 respectively; FIG. 16).

Overall, this data indicates that NISV and gNISV delivery of Hu1A3B-7 VEEV mAb is advantageous compared to free mAb. Both platforms reduce viral load in the lung, and increase survival and reduce morbidity. Significantly, the gNISV platform reduces viral load in the brain. This would suggest that the vesicles specifically designed to deliver cargo such as pharmaceutical agents to the brain are capable of targeting this tissue and delivering therapeutically-relevant concentrations of cargo.

It will be understood that the present invention has been described above purely by way of example, and modification of detail can be made within the scope of the invention. Each feature disclosed in the description, and (where appropriate) the claims, may be provided independently or in any appropriate combination. Moreover, the invention has been described with specific reference to methods, pharmaceutical composition and associated kits, and more specifically with reference to pharmaceutical-vesicle formulations and associated pharmaceutical kits for use against B. pseudomallei, F. tularensis and VEEV. Additional applications of the invention will occur to the skilled person.

The invention claimed is:

1. A method for the preparation of a pharmaceutical-vesicle formulation, the method comprising the steps of:
   a) heating vesicle components comprising monopalmitoyl glycerol, cholesterol and dicetyl phosphate at a temperature in the range of 50° C. to 150° C.;
   b) dissolving a pharmaceutical agent in a pharmaceutically-acceptable carrier and heating the resultant pharmaceutical agent-carrier mixture at a range of 30-99° C.;
   adding the pharmaceutical agent-carrier mixture to the vesicle components to provide a formulation mixture; and,
   d) processing the formulation mixture to form a pharmaceutical-vesicle formulation, whereby the pharmaceutical agent and carrier is entrapped within a plurality of vesicles
   wherein the pharmaceutical agent is an orally-available antibiotic,
   wherein the pharmaceutical-vesicle formulation is reconstituted in a known quantity of the pharmaceutical agent dissolved in a pharmaceutically-acceptable carrier to provide a biphasic pharmaceutical-vesicle formulation,
   wherein the vesicles are modified with i) glucosamine and/or ii) transferrin,
   wherein, for i), palmitic acid is covalently linked to the glucosamine to provide palmitoylated glucosamine, and
   wherein, for ii), cholesterol is modified by replacing a portion of the cholesterol by, cholesterol-PEG-malemide, and the vesicle components further comprise thiolated transferrin, or any variant which is at least 70% identical to transferrin wild-type or base sequence, or any fragment which is any amino acid portion which retains the desired properties of transferrin wild-type or base sequence, such that a covalent bond forms between the thiolated transferrin, or variant or fragment, and the modified cholesterol.

2. The method according to claim 1, wherein the monopalmitoyl glycerol, cholesterol and dicetyl phosphate are provided in a 5:4:1 molar ratio respectively.

3. The method according to claim 1, wherein sodium deoxycholate is provided in the vesicle components and/or when dissolving a pharmaceutical agent in a pharmaceutically-acceptable carrier.

4. The method according to claim 1, wherein the pharmaceutical agent-carrier mixture and vesicle components are provided in a respective ratio of 3:1.

5. The method according to claim 1, wherein the pharmaceutical-vesicle formulation undergoes at least one freeze-drying and thawing cycle following processing.

6. The method according to claim 1, wherein the antibacterial agent is selected from a group consisting of fluoroquinolones and tetracyclines.

7. The method according to claim 1, wherein the antibacterial agent is selected from a group consisting of levofloxacin, ciprofloxacin and doxycycline.

8. The method according to claim 1, wherein the antibacterial agent is at a concentration of 30 mg/ml.

9. A pharmaceutical-vesicle formulation prepared by the method of claim 1.

10. The pharmaceutical-vesicle formulation according to claim 9, wherein the monopalmitoyl glycerol, cholesterol and dicetyl phosphate are present in a 5:4:1 molar ratio respectively.

11. The pharmaceutical-vesicle formulation according to claim 9, wherein the vesicle is of a size of 50-4000 nm.

12. The pharmaceutical-vesicle formulation according to claim 9, wherein the antibacterial agent is selected from a group consisting of fluoroquinolones and tetracyclines.

13. The pharmaceutical-vesicle formulation according to claim 12, wherein the antibacterial agent is selected from a group consisting of levofloxacin, ciprofloxacin and doxycycline.

14. The pharmaceutical-vesicle formulation according to claim 9, wherein the antibacterial agent is present at concentration of 30 mg/ml.

15. A pharmaceutical kit comprising the pharmaceutical-vesicle formulation of claim 9.

16. The method according to claim 1, wherein, for ii), a ratio of cholesterol to cholesterol-PEG-malemide is 4:1.

17. The pharmaceutical-vesicle formulation according to claim 9, wherein, for ii), a ratio of cholesterol to cholesterol-PEG-malemide is 4:1.

18. The pharmaceutical-vesicle formulation according to claim 9, wherein sodium deoxycholate is provided in the vesicle components and/or when dissolving a pharmaceutical agent in a pharmaceutically-acceptable carrier.

19. The pharmaceutical-vesicle formulation according to claim 9, wherein the pharmaceutical agent-carrier mixture and vesicle components are provided in a respective ratio of 3:1.

* * * * *

UNITED STATES PATENT AND TRADEMARK OFFICE
CERTIFICATE OF CORRECTION

| | |
|---|---|
| PATENT NO. | : 11,524,080 B2 |
| APPLICATION NO. | : 17/273059 |
| DATED | : December 13, 2022 |
| INVENTOR(S) | : Ethel Diane Williamson et al. |

It is certified that error appears in the above-identified patent and that said Letters Patent is hereby corrected as shown below:

In the Claims

Column 31, Line 36, Claim 1, replace "adding the pharmaceutical agent-carrier mixture to the" with -- c) adding the pharmaceutical agent-carrier mixture to the --

Column 31, Line 56, Claim 1, replace "portion of the cholesterol by, cholesterol-PEG-male-" with -- portion of the cholesterol by cholesterol-PEG-male- --

Signed and Sealed this
Fifth Day of September, 2023

Katherine Kelly Vidal
*Director of the United States Patent and Trademark Office*